(12) United States Patent
Kowalewski et al.

(10) Patent No.: US 10,760,597 B2
(45) Date of Patent: Sep. 1, 2020

(54) SOFT ROBOTS, SOFT ACTUATORS, AND METHODS FOR MAKING THE SAME

(71) Applicant: Regents of the University of Minnesota, Minneapolis, MN (US)

(72) Inventors: Timothy Mariusz Kowalewski, Saint Paul, MN (US); James Donald Van de Ven, Long Lake, MN (US); Mark David Gilbertson, Burnsville, MN (US); Gabriel Ray Crooks Korinek, Minneapolis, MN (US); Gillian Jo McDonald, New Brighton, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 197 days.

(21) Appl. No.: 15/569,958

(22) PCT Filed: Apr. 27, 2016

(86) PCT No.: PCT/US2016/029584
§ 371 (c)(1),
(2) Date: Oct. 27, 2017

(87) PCT Pub. No.: WO2016/176340
PCT Pub. Date: Nov. 3, 2016

(65) Prior Publication Data
US 2019/0032684 A1    Jan. 31, 2019

Related U.S. Application Data

(60) Provisional application No. 62/153,165, filed on Apr. 27, 2015.

(51) Int. Cl.
*B25J 9/06* (2006.01)
*F15B 15/10* (2006.01)
(Continued)

(52) U.S. Cl.
CPC .............. *F15B 15/10* (2013.01); *A61B 34/30* (2016.02); *A61M 25/0012* (2013.01);
(Continued)

(58) Field of Classification Search
CPC .......... F15B 15/10; F15B 11/20; F15B 13/08; A61M 25/0012; A61M 25/0116;
(Continued)

(56) References Cited

U.S. PATENT DOCUMENTS

| 5,113,911 A | 5/1992 | Hirsch |
| 2006/0084964 A1 | 4/2006 | Knudson et al. |

(Continued)

FOREIGN PATENT DOCUMENTS

| CN | 202910862 U | 5/2013 |
| CN | 104227721 A | 12/2014 |
| WO | 2012148472 A2 | 11/2012 |

OTHER PUBLICATIONS

International Search Report and Written Opinion for Application No. PCT/US2016/029584 dated Oct. 26, 2016 (12 pgs).
(Continued)

*Primary Examiner* — Abiy Teka
(74) *Attorney, Agent, or Firm* — Dicke, Billig & Czaja, PLLC

(57) ABSTRACT

A material-mapped actuator useful as, or as part of, a soft robot along with automated methods of design and manufacture. The actuator exhibits mechanical properties that spatially vary along a coordinate system of the actuator. The actuator body has an initial shape with a corresponding initial map of mechanical attributes consisting of locally-varying stiffness at each point in a volume of the actuator body. The actuator is configured to change to a different shape or distribution of mechanical properties upon being activated by an actuation medium. The map of mechanical
(Continued)

attributes influences and determines the new shape or distribution. The material-mapped actuator can incorporate a spatially-varying distribution of mechanical properties that dictates multiple desired shapes as the actuation medium is applied, including an actuation sequence in which the actuator transitions from a first shape to a desired intermediate shape(s), and from the intermediate shape to a desired final shape.

11 Claims, 22 Drawing Sheets

(51) Int. Cl.

| | | |
|---|---|---|
| B25J 18/06 | (2006.01) | |
| B25J 18/02 | (2006.01) | |
| B25J 9/14 | (2006.01) | |
| A61B 34/30 | (2016.01) | |
| A61M 25/00 | (2006.01) | |
| A61M 25/01 | (2006.01) | |
| F15B 11/20 | (2006.01) | |
| F15B 13/08 | (2006.01) | |
| E21B 7/04 | (2006.01) | |

(52) U.S. Cl.
CPC .......... *A61M 25/0116* (2013.01); *B25J 9/065* (2013.01); *B25J 9/142* (2013.01); *B25J 18/02* (2013.01); *B25J 18/06* (2013.01); *F15B 11/20* (2013.01); *F15B 13/08* (2013.01); *A61B 2034/301* (2016.02); *A61B 2034/303* (2016.02); *B25J 9/14* (2013.01); *E21B 7/04* (2013.01); *F15B 2211/3059* (2013.01); *F15B 2211/71* (2013.01); *F15B 2211/78* (2013.01); *F15B 2215/30* (2013.01)

(58) Field of Classification Search
CPC .. B25J 18/06; B25J 9/142; B25J 18/02; A61B 34/30
See application file for complete search history.

(56) References Cited

U.S. PATENT DOCUMENTS

| | | |
|---|---|---|
| 2010/0010437 A1 | 1/2010 | Miles et al. |
| 2015/0001994 A1 | 1/2015 | Ahn et al. |
| 2015/0040753 A1 | 2/2015 | Bishop-Moser et al. |
| 2015/0090113 A1 | 4/2015 | Galloway |
| 2015/0266186 A1* | 9/2015 | Mosadegh ............... B25J 9/142 92/34 |

OTHER PUBLICATIONS

Allison, James et al. "Design of Engineering Systems in Industrial and Enterprise Systems Engineering Department at University of Illinois", 2014 International Engineering Systems Symposium, 8 pgs.

Bishop-Moser, Joshua et al., "Design of Soft Robotic Actuators using Fluid-filled Fiber-Reinforced Elastomeric Enclosures in Parallel Combinations", 2012 IEEE/International Conference on Intelligent Robots and Systems, Oct. 7-12, 2012, pp. 4264-4269.

Bishop-Moser, Joshua et al., "Towards Snake-like Soft Robots: Design of Fluidic Fiber-Reinforced Elastomeric Helical Manipulators", 2013 IEEE/International Conference on Intelligent Robots and Systems, Nov. 3-7, 2013, pp. 5021-5026.

De Greef, Aline et al., "Towards flexible medical instruments: Review of flexible fluidic actuators", 2008, Precision Engineering, pp. 311-321.

Fu, Yili et al., "Steerable catheters in minimally invasive vascular surgery", Sep. 2009, The International Journal of Medical Robotics and Computer Assisted Surgery, 11 pgs.

Ikuta, Koji et al., "Multi-degree of Freedom Hydraulic Pressure Driven Safety Active Catheter", May 2006, Proceedings of the 2006 IEEE International Conference on Robotics and Automation, pp. 4161-4166.

Thrust 2: Compactness, 2F.1: Soft Pneumatic Actuator for Arm Orthosis, http://www.ccefp.org/research/thrust-2-compactness/ project, retrieved on Jan. 14, 2015, 1 pg.

Yajima, Daisuke et al., "Study on Hydraulically-Driven Active Catheter for Safe Operation", 2011, The Japan Society of Mechanical Engineers, 10 pgs.

* cited by examiner

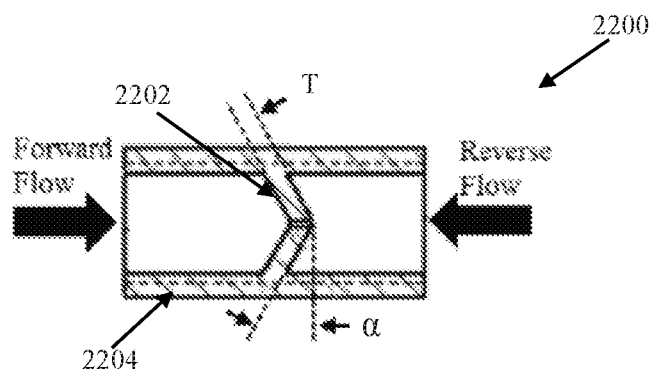
FIG. 20A
FIG. 20B
| | Valve Thickness | | | | | | | |
|---|---|---|---|---|---|---|---|---|
| | 0.050" | | 0.075" | | 0.100" | | 0.150" | |
| Angle | $P_{fwd}$ | $P_{rev}$ | $P_{fwd}$ | $P_{rev}$ | $P_{fwd}$ | $P_{rev}$ | $P_{fwd}$ | $P_{rev}$ |
| 0° | 3.0 | 3.0 | 7.3 | 7.3 | 12.6 | 12.6 | 15.0 | 15.0 |
| 10° | 3.0 | 5.8 | 5.2 | 9.8 | 10.6 | 15.5 | 12.3 | 15.6 |
| 20° | 3.1 | 5.3 | 7.6 | 12.1 | 8.6 | 16.5 | 11.5 | 17.5 |
| 30° | 2.7 | 5.6 | 2.4 | 11.3 | 7.1 | 17.8 | 9.3 | 19.8 |
| 40° | 2.4 | 5.3 | 2.6 | 12.8 | 4.1 | 17.8 | 7.0 | 20.1 |
| 50° | 2.8 | 4.9 | 2.5 | 6.8 | 4.0 | 17.9 | 6.4 | 20.8 |
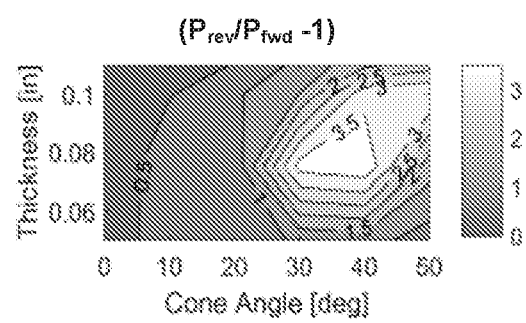
FIG. 20C

SOFT ROBOTS, SOFT ACTUATORS, AND METHODS FOR MAKING THE SAME

CROSS-REFERENCE TO RELATED APPLICATIONS

This Utility Patent Application claims priority under 35 U.S.C. § 371 to International Application Serial No. PCT/US2016/029584, filed Apr. 27, 2016, which claims the benefit of Provisional Patent Application No. 62/153,165, filed Apr. 27, 2015; which are both incorporated herein by reference in their entirety.

BACKGROUND

Conventional robots are sometimes stiff and might not be suitable for moving through passages, such as passages that might have bends. Moreover, such robots might not be suitable for use in arteries in a living organism, such as a human body, in that such robots could possibly puncture artery walls.

More recently, fiber-reinforced elastomeric enclosure (FREE) actuators have been contemplated for possible use with or as a "soft" robot. FREEs are described in U.S. Application Publication No. 2015/0040753 (Bishop-Moser et al.), and entail one or more continuous fibers applied to a length of a hollow elastomeric cylinder in a helical pattern having a constant or uniform pitch. In the presence of a fluid medium, the FREE actuator experiences uniform change in shape. While the described FREE actuators appear promising for potential soft robot applications, the physical constraints presented by many soft robot usage environments may not be fully addressed.

SUMMARY

The inventors of the present disclosure recognized that a need exists for actuators, soft robots, and methods of designing and making actuators and soft robots that overcome one or more of the above-mentioned problems.

Some aspects of the present disclosure are directed toward a material-mapped actuator useful as or as part of a soft robot. The actuator exhibits mechanical properties that spatially vary along a coordinate system of the actuator. The actuator includes an actuator body that has an initial shape with a corresponding initial map of mechanical attributes consisting of locally-varying stiffness at each point in a volume of the actuator body. Further, the actuator body is configured to change to a new, different shape or different distribution of mechanical properties upon being activated by an actuation medium. The initial spatially-varying map of mechanical attributes influences and determines the new shape or distribution. In some embodiments, the actuator includes a material applied to a tubular body, such as locally-oriented fibers, meshes, threads, etc. that induce desired material anisotropies and strain limiting behaviors where the fiber orientation of pitch is free to vary in any direction along the actuator body. In other embodiments, the material-mapped actuator incorporates a spatially-varying distribution of mechanical properties that dictates multiple desired shapes as the actuation medium is applied, including, for example, an actuation sequence in which the actuator transitions from a first shape to one or more desired intermediate shapes, and from the desired intermediate shape(s) to a desired final shape.

Other aspects of the present disclosure are directed toward a method for making a soft robot for performing a specified procedure or task. The method include receiving procedure-related information indicative of at least a desired initial shape and a desired final shape, and optionally one or more desired intermediate shapes, of the soft robot in preforming the procedure. Design parameters for one or more material-mapped actuators are determined based upon the received procedure-related information, and one or more material-mapped actuators are formed as a function of the determined design parameters. The inverse design techniques of the present disclosure can optionally further include generating a manufacturing blueprint based upon material mapping, for example by operating a dithering algorithm.

Yet other aspects of the present disclosure are directed toward systems for manufacturing a soft robot consisting of one or more actuators. The system includes a mapping module and a manufacturing module. The mapping module includes a computing device operating on computer instructions to generate material mapping and manufacturing blueprint information. The manufacturing module is operated in accordance with the manufacturing blueprint information to generate one or more material-mapped actuators, such as by an additive or subtractive process.

BRIEF DESCRIPTION OF THE DRAWINGS

FIG. 20A is a cross-sectional diagram of an asymmetric passive valve useful with soft robots of the present disclosure.

FIG. 20B is a table of forward and reverse direction flow pressure of the valve of FIG. 20A at different cone angles and thicknesses.

FIG. 20C is a contour plot of pressure ratios provided by the valve of FIG. 20A at different cone angles and thicknesses.

DETAILED DESCRIPTION

Figure 1A:
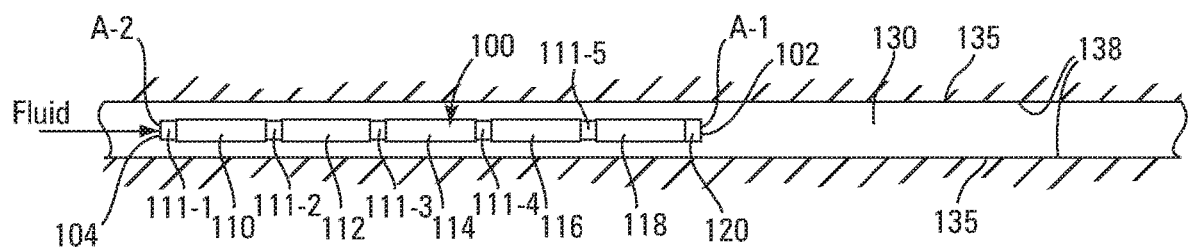
FIGS. 1A-1F illustrate examples of different configurations of a robot during motion of the robot.

FIGS. 1A-1F illustrate different configurations of a robot 100 in accordance with principles of the present disclosure and during motion of robot 100. In FIG. 1A, robot 100 is in an initial, unactuated state and is at an initial location, where a distal end 102 of robot 100 is at a point A-1 and a proximal end 104 of robot 100 is at a point A-2. In general, FIGS. 1A-1F show the different configuration states of robot 100 as robot 100 moves from its initial location in FIG. 1A to a location in FIG. 1F, where distal end 102 is at a point D and proximal end 104 is at a point C-2.

In some examples, robot 100 might be referred to as a "soft" (e.g., a soft catheter) robot that can conform to the shape of a flow passage, e.g., the flow passage in an artery in a living organism, such as a human body, e.g., without damaging the wall of the artery. For example, robot 100 might be formed from elastomers (e.g., silicone, thermoplastic elastomers, isoprenes, rubber, latex, etc.) that might be reinforced with fibers (nylon, woven carbon fibers, etc.) or that might include elastomers having different stiffnesses and/or different thicknesses that allow robot 100 to conform to the different shapes of different flow passages.

Figure 1B:
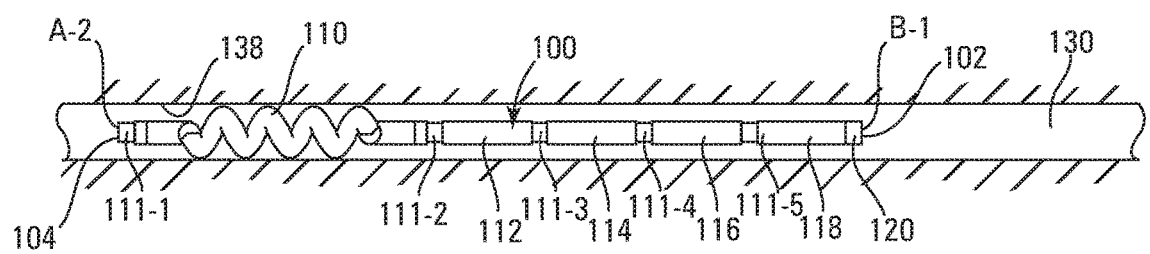

Robot 100 includes a section or actuator 110 that has a hollow core, e.g., a flow passage. Section 110 may be a circular tube, for example. Section 110 is configured to become a spiral (e.g., a section 110 spiral), as shown in FIG. 1B, in response to a pressure of a fluid (e.g., that might be called a working fluid), such as water, saline, etc., within the hollow core of section 110. For example, section 110 becomes a spiral in response to the hollow core of section 110 selectively receiving the working fluid from a fluid pressure source (e.g., an upstream pressure source), such as a pump (e.g. a piston-cylinder pump, a syringe, etc.) through a valve 111-1, e.g., when valve 111-1 is actuated to an open (e.g., a fully open) state.

Valve 111-1 is between proximal end 104 and section 110. Valve 111-1 selectively fluidly couples the hollow core of section 110 to the fluid pressure source that may be upstream of valve 111-1. Note that section 110 in FIG. 1A is transformed into the spiral in FIG. 1B in response to the hollow core of section 110 selectively receiving the fluid from the pressure source. Selectively receiving a fluid as used herein, for example, means receiving the fluid in response to an action, such as the opening of valve 111-1.

In some examples, valve 111-1 might be actuated by the working fluid, whereas in other examples valve 111-1 might be actuated by a pilot fluid (e.g., having the same composition as the working fluid) being directed to valve 111-1 by a pilot line. Note that the term "pilot fluid" is used to denote fluid that flows through pilot lines.

Valve 111-1 might be a multi-stage pressure-relief valve, for example, that is actuated into an open state in response to the pressure of the working fluid upstream of valve 111-1 reaching a certain pressure level, at which point the working fluid enters section 110. In some examples, where valve 111-1 is opened by the pressure of the working fluid upstream of valve 111-1 reaching a certain pressure level, section 110 might become a spiral in response to that certain pressure level.

Valve 111-1 might be actuated into a closed state in response to a further increase in the pressure of the working fluid upstream of valve 111-1, or, alternatively, in response to a decrease in the pressure of the working fluid upstream of valve 111-1. In some examples, valve 111-1 might be opened in response to a pressure of the pilot fluid in a pilot line reaching a certain pressure level and might be closed in response to a pressure of the pilot fluid in the pilot line reaching a certain other pressure level, e.g., that might be greater than or less than the pressure of the pilot fluid that opens valve 111-1.

In some examples, valve 111-1 might open (e.g., fully open) in response to the pressure of the working fluid upstream of valve 111-1 fluctuating (e.g., oscillating) at a certain frequency (e.g., at a resonant frequency of valve 111-1) and might close in response to the pressure of the working fluid upstream of valve 111-1 fluctuating at a certain other frequency (e.g., at a non-resonant frequency of valve 111-1). In other examples, valve 111-1 might open in response to the pressure of the pilot fluid in the pilot line fluctuating at a certain frequency (e.g., at a resonant frequency of valve 111-1) and might close in response to the pilot fluid in the pilot line fluctuating at a certain other frequency (e.g., at a non-resonant frequency of valve 111-1).

A section or actuator 112 has a hollow core, e.g., a flow passage, that is selectively fluidly coupled in series with the hollow core of section 110. Section 112 may be a circular tube, for example. A valve 111-2 that is between section 110 and section 112 selectively fluidly couples the hollow core of section 110 in series with the hollow core of section 112.

As used herein "fluidly coupled" means to allow the flow of fluid. For example, fluid is allowed to flow between the fluidly coupled hollow cores of sections 110 and 112, e.g., from the hollow core of section 110 to the hollow core of section 112. For selectively fluidly coupled hollow cores, fluid flows from the hollow core of section 110 to the hollow core of section 112 in response to an action, such as the opening of the valve 111-2 between the hollow core of section 110 and the hollow core of section t 112. That is, for example, when a valve is between two hollow cores, the two hollow cores are selectively fluidly coupled to each other.

Figure 1C:
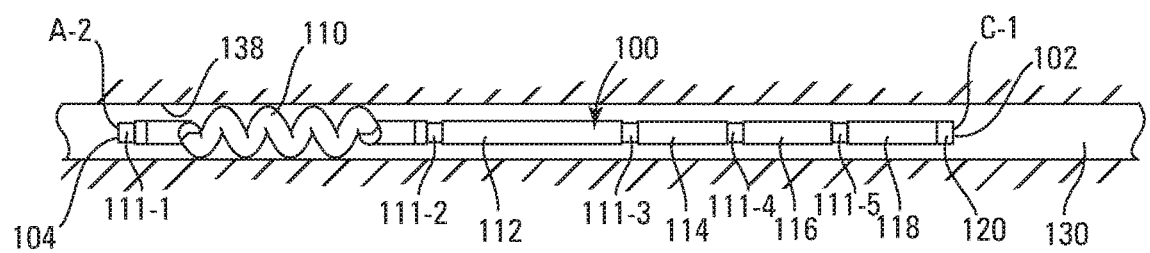

Section 112 is configured to extend, as shown in FIG. 1C, in response to a pressure of a fluid within the hollow core of section 112. For example, section 112 extends in response to the hollow core of section 112 selectively receiving the working fluid from section 110 through a valve 111-2, e.g., when valve 111-2 is actuated to an open (e.g., a fully open)

state. Section 112 in extends from the length in FIG. 1B to the length in FIG. 1C in response to the hollow core of section 112 selectively receiving the working fluid from the hollow core of section 110.

In some examples, valve 111-2 might be actuated by the working fluid, whereas in other examples valve 111-2 might be actuated by the pilot fluid being directed to valve 111-2 by a pilot line. Valve 111-2 might be a multi-stage pressure-relief valve, for example, that is actuated into an open state in response to the pressure of the working fluid upstream of valve 111-2 in section 110 reaching a certain pressure level, e.g., that might be greater than the pressure level that opened valve 111-1, at which point the working fluid enters section 112.

In some examples, where valve 111-2 is opened by the pressure of the working fluid upstream of valve 111-2 reaching a certain pressure level, section 112 might extend in response to that certain pressure level. Valve 111-2 might be actuated into a closed state in response to a further increase in the pressure of the working fluid upstream of valve 111-2, or, alternatively, in response to a decrease in the pressure of the working fluid upstream of valve 111-2. In some examples, valve 111-2 might be opened in response to a pressure of the pilot fluid in a pilot line reaching a certain pressure level and might be closed in response to a pressure of the pilot fluid in the pilot line reaching a certain other pressure level, e.g., that might be greater than or less than the pressure of the pilot fluid that opens valve 111-2.

In some examples, valve 111-2 might open (e.g., fully open) in response to the pressure of the working fluid upstream of valve 111-2 fluctuating (e.g., oscillating) at a certain frequency (e.g., at a resonant frequency of valve 111-2) and might close in response to the pressure of the working fluid upstream of valve 111-2 fluctuating at a certain other frequency (e.g., at a non-resonant frequency of valve 111-2). In other examples, valve 111-2 might open in response to the pressure of the pilot fluid in the pilot line fluctuating at a certain frequency (e.g., at a resonant frequency of valve 111-2) and might close in response to the pilot fluid in the pilot line fluctuating at a certain other frequency (e.g., at a non-resonant frequency of valve 111-2).

A section or actuator 114 has a hollow core, e.g., a flow passage, that is selectively fluidly coupled in series with the hollow core of section 112. Section 114 may be a circular tube, for example. A valve 111-3 that is between section 112 and section 114 selectively fluidly couples the hollow core of section 112 in series with the hollow core of section 114.

Figure 1D:
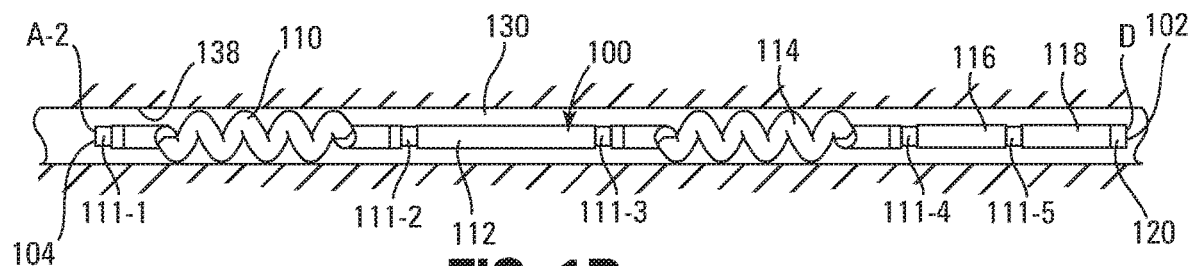

Section 114 is configured to become a spiral (e.g., a section 114 spiral), as shown in FIG. 1D, in response to a pressure of a fluid within the hollow core of section 114. For example, the hollow core of section 114 selectively receives the working fluid from the hollow core of section 112 through a valve 111-3, e.g., when valve 111-3 is actuated to an open (e.g., a fully open) state. Note that section 114 in FIG. 1C is transformed into the spiral in FIG. 1D in response to the hollow core of section 114 selectively receiving the working fluid from section 112.

In some examples, valve 111-3 might be actuated by the working fluid, whereas in other examples valve 111-3 might be actuated by the pilot fluid being directed to valve 111-3 by a pilot line. Valve 111-3 might be a multi-stage pressure-relief valve, for example, that is actuated into an open state in response to the pressure of the working fluid upstream of valve 111-3 in section 112 reaching a certain pressure level, e.g., that might be greater than the pressure level that opened valve 111-2, at which point the working fluid enters section 114.

In some examples, where valve 111-3 is opened by the pressure of the working fluid upstream of valve 111-3 reaching a certain pressure level, section 114 might become a spiral in response to that certain pressure level. Valve 111-3 might be actuated into a closed state in response to a further increase in the pressure of the working fluid upstream of valve 111-3, or, alternatively, in response to a decrease in the pressure of the working fluid upstream of valve 111-3. In some examples, valve 111-3 might be opened in response to a pressure of the pilot fluid in the pilot line reaching a certain pressure level and might be closed in response to a pressure of the pilot fluid in the pilot line reaching a certain other pressure level, e.g., that might be greater than or less than the pressure of the pilot fluid that opens valve 111-3.

In some examples, valve 111-3 might open (e.g., fully open) in response to the pressure of the working fluid upstream of valve 111-3 fluctuating (e.g., oscillating) at a certain frequency (e.g., at a resonant frequency of valve 111-3) and might close in response to the pressure of the working fluid upstream of valve 111-3 fluctuating at a certain other frequency (e.g., at a non-resonant frequency of valve 111-3). In other examples, valve 111-3 might open in response to the pressure of the pilot fluid in the pilot line fluctuating at a certain frequency (e.g., at a resonant frequency of valve 111-3) and might close in response to the pilot fluid in the pilot line fluctuating at a certain other frequency (e.g., at a non-resonant frequency of valve 111-3).

A section or actuator 116 has a hollow core, e.g., a flow passage, that is selectively fluidly coupled in series with the hollow core of section 114. A valve 111-4 that is between section 114 and section 116 selectively fluidly couples the hollow core of section 114 in series with the hollow core of section 116.

Section 116 is configured to twist in response to a pressure of a fluid within the hollow core of section 116. For example, section 116 twists in response to the hollow core of section 116 selectively receiving the fluid from section 114 through valve 111-4, e.g., when valve 111-4 is actuated to an open state.

Figure 2A:
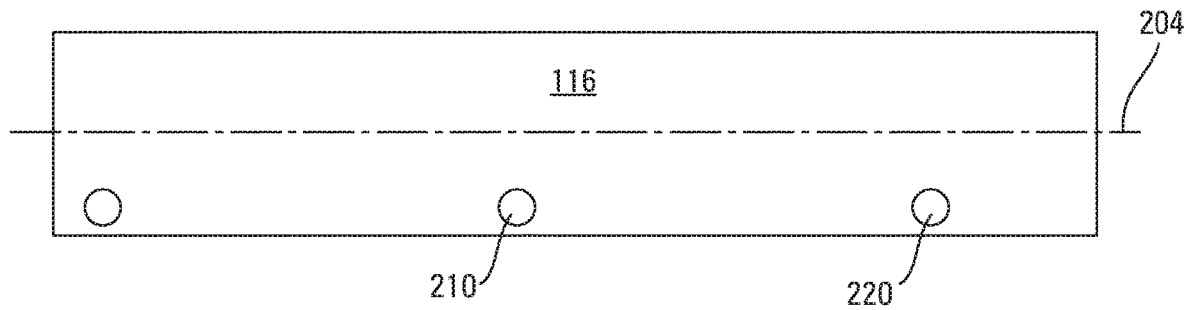
FIGS. 2A and 2B illustrate an example of twisting a section of a robot.
Figure 2B:
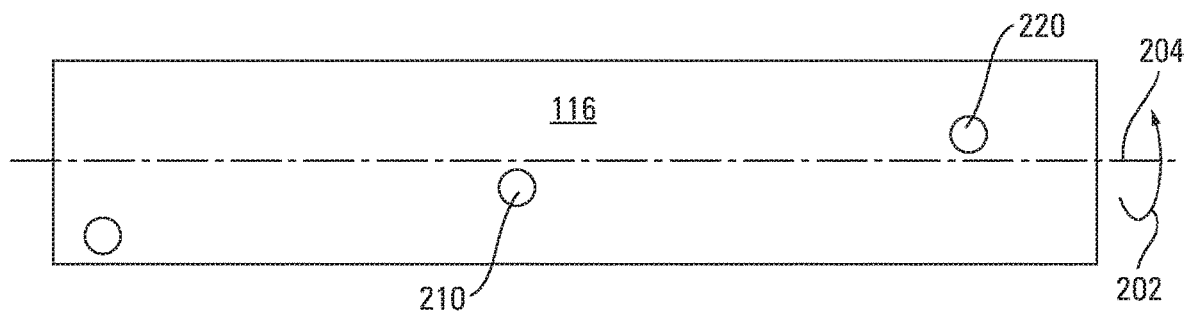

FIGS. 2A and 2B illustrate the twisting of section 116. FIG. 2A shows section 116 in an untwisted state, and FIG. 2B illustrates section 116 after twisting. FIGS. 2A and 2B show that twisting in the direction of arrow 202 about the central axis 204 of section 116 displaces open circles 210 and 220 from their respective locations in FIG. 2A to their respective locations in FIG. 2B. Note that the twisting does not affect the orientation of the central axis 204.

In some examples, valve 111-4 might be actuated by the working fluid, whereas in other examples valve 111-4 might be actuated by the pilot fluid being directed to valve 111-4 by a pilot line. Valve 111-4 might be a multi-stage pressure-relief valve, for example, that is actuated into an open (e.g., a fully open) state in response to the pressure of the working fluid upstream of valve 111-4 in section 114 reaching a certain pressure level, e.g., that might be greater than the pressure level that opened valve 111-3, at which point the working fluid enters section 116.

In some examples, where valve 111-4 is opened by the pressure of the working fluid upstream of valve 111-4 reaching a certain pressure level, section 116 might twist in response to that certain pressure level. Valve 111-4 might be actuated into a closed state in response to a further increase in the pressure of the working fluid upstream of valve 111-4, or, alternatively, in response to a decrease in the pressure of the working fluid upstream of valve 111-4. In some examples, valve 111-4 might be configured to be partially opened by different amounts, e.g., between the closed and fully open states, in response to respectively varying the pressure of the working fluid upstream of valve 111-4.

In some examples, valve 111-4 might be opened (e.g., fully opened) in response to a pressure of the pilot fluid in the pilot line reaching a certain pressure level and might be closed in response to a pressure of the pilot fluid in the pilot line reaching a certain other pressure level, e.g., that might be greater than or less than the pressure of the pilot fluid that opens valve 111-4. The valve 111-4 might be configured to be partially opened by different amounts, e.g., between the closed and fully open states, in response to respectively varying the pressure of the pilot fluid.

In some examples, valve 111-4 might fully open in response to the pressure of the working fluid upstream of valve 111-4 fluctuating (e.g., oscillating) at a certain frequency (e.g., at a resonant frequency of valve 111-4) and might close in response to the pressure of the working fluid upstream of valve 111-4 fluctuating at a certain other frequency (e.g., at a non-resonant frequency of valve 111-4). In other examples, valve 111-4 might fully open in response to the pressure of the pilot fluid in the pilot line fluctuating at a certain frequency (e.g., at a resonant frequency of valve 111-4) and might close in response to the pilot fluid in the pilot line fluctuating at a certain other frequency (e.g., at a non-resonant frequency of valve 111-4). In some examples, the valve 111-4 might be configured to be partially opened by different amounts between the fully open and closed states in response to the working fluid or the pilot fluid respectively fluctuating by different frequencies that might be between the frequency that closes valve 111-4 and the frequency that fully opens valve 111-4.

A section or actuator 118 has a hollow core, e.g., a flow passage, that is selectively fluidly coupled in series with the hollow core of section 116. A valve 111-5 that is between section 116 and section 118 selectively fluidly couples the hollow core of section 116 in series with the hollow core of section 118.

Section 118 is configured to bend in response to a pressure of a fluid within the hollow core of section 118. For example, section 118 bends in response to the hollow core of section 118 selectively receiving the fluid from section 116 through valve 111-5, e.g., when valve 111-5 is actuated to an open (e.g., a fully open) state.

Figure 3A:
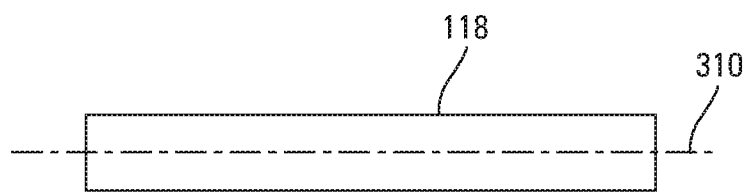
FIGS. 3A and 3B illustrate an example of bending a section of a robot.
Figure 3B:
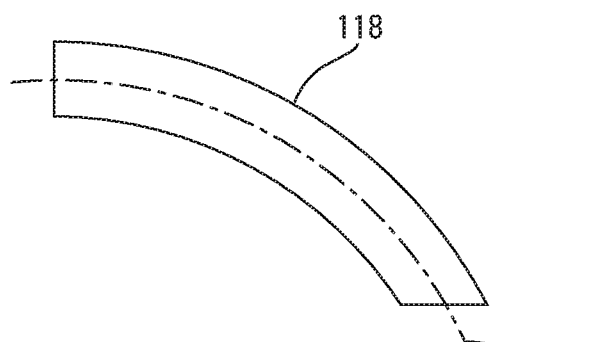

FIGS. 3A and 3B illustrate the bending of section 118. FIG. 3A shows section 118 in a straight, unbent state, and FIG. 3B illustrates section 118 after bending. It is seen that the central axis 310 of section 118 follows the bend in FIG. 3B.

In some examples, valve 111-5 might be actuated by the working fluid, whereas in other examples valve 111-5 might be actuated by the pilot fluid being directed to valve 111-5 by a pilot line. Valve 111-5 might be a multi-stage pressure-relief valve, for example, that is actuated into a fully open state in response to the pressure of the working fluid upstream of valve 111-5 in section 116 reaching a certain pressure level, e.g., that might be greater than the pressure level that opened valve 111-4, at which point the working fluid enters section 118.

In some examples, where valve 111-5 is fully opened by the pressure of the working fluid upstream of valve 111-5 reaching a certain pressure level, section 118 might bend in response to that certain pressure level. Valve 111-5 might be actuated into a closed state in response to a further increase in the pressure of the working fluid upstream of valve 111-5, or, alternatively, in response to a decrease in the pressure of the working fluid upstream of valve 111-5. In some examples, valve 111-5 might be configured to be partially opened by different amounts, e.g., between the closed and fully open states, in response to respectively varying the pressure of the working fluid upstream of valve 111-5.

In some examples, valve 111-5 might be fully opened in response to a pressure of the pilot fluid in the pilot line reaching a certain pressure level and might be closed in response to a pressure of the pilot fluid in the pilot line reaching a certain other pressure level, e.g., that might be greater than or less than the pressure that opens valve 111-5. The valve 111-5 might be configured to be partially opened by different amounts, e.g., between the closed and fully open states, in response to respectively varying the pressure of the pilot fluid.

In some examples, valve 111-5 might fully open in response to the pressure of the working fluid upstream of valve 111-5 fluctuating (e.g., oscillating) at a certain frequency (e.g., at a resonant frequency of valve 111-5) and might close in response to the pressure of the working fluid upstream of valve 111-5 fluctuating at a certain other frequency (e.g., at a non-resonant frequency of valve 111-5). In other examples, valve 111-5 might fully open in response to the pressure of the pilot fluid in the pilot line fluctuating at a certain frequency (e.g., at a resonant frequency of valve 111-5) and might close in response to the pilot fluid in the pilot line fluctuating at a certain other frequency (e.g., at a non-resonant frequency of valve 111-5). In some examples, the valve 111-5 might be configured to be partially opened by different amounts between the fully open and closed states in response to the working fluid or the pilot fluid respectively fluctuating by different frequencies that might be between the frequency that closes valve 111-5 and the frequency that fully opens valve 111-5.

A section or actuator 120 is between section 118 and distal end 102. For example section 120 might be referred to as a tip 120 of robot 100, as shown in FIGS. 1A-1F. Section 120 might be configured as a sensor and/or an actuator in some examples. The sensor, for example, might be exposed at distal end 102. For example, section 120 might be configured to sense the presence of a target material that may or may not be distinct from a wall, such as a wall of an artery (e.g., in the living organism, such as the human body), and/or might be configured to remove the target material. For example, the target material might be plaque on an artery wall. For example, section 120 might include sensing fibers, e.g., that may be exposed at distal end 102, that can sense the presence of the target material, such as plaque, and/or fiber optics, e.g., that may be exposed at distal end 102, that can deliver laser (excimer laser) pulses to the sensed target material to remove the sensed target material. Distal end 102 may be brought into contact, with the target material on a wall of an artery for sensing and/or removing the target material.

In some examples, section 120 might include a vibrator that while vibrating facilitates movement (e.g., burrowing) of robot 110 through a medium, such as dirt, sand, debris, etc. Distal end 102 may be closed to (e.g., may be configured to block) the flow of the working fluid.

The examples of FIGS. 1A to 1F show the movement of robot 100 through an opening 130, such as the opening in an artery. The opening 130 is bounded by a wall 135, as shown in FIG. 1A, having internal bounding surface 138, as shown in FIGS. 1A-1F. Alternatively, for examples where robot 100 is configured to burrow through a medium, opening 130 and its bounding wall 135 would be replaced by the medium, so the medium surrounds robot 100.

In FIG. 1B, section 110 is transformed from its shape in FIG. 1A to a spiral (e.g., a section 110 spiral) in response to the hollow core of section 110 selectively receiving the working fluid so that the spiral exerts a force on bounding surface 138 sufficient to prevent the spiral from moving. For examples involving burrowing through the medium, the section 110 spiral might extend into the surrounding medium to prevent the section 110 spiral from moving. In some examples, a fluid, such as blood, might be flowing through opening 130. The section 110 spiral allows the fluid to flow past the exterior of the spiral, e.g., though the center of the coils of the section 110 spiral, without stopping the flow of the fluid.

Section 110 is transformed from its initial shape in FIG. 1A to the section 110 spiral in FIG. 1B in response to valve 111-1 being actuated to an open state while valves 111-2 and 111-3 are closed, for example. For example, section 110 is transformed into the section 110 spiral in response to the pressure of the received fluid within the hollow core of section 110. Note, for example, that the transformation of section 110 into the section 110 spiral can cause section 110 to extend to a length that is greater than the length of section 110 in FIG. 1A, thereby causing distal end 102 to move from point A-1 in FIG. 1A to point B-1 in FIG. 1B. For example, section 110 might extend while section 110 is being transformed into the section 110 spiral.

In FIG. 1C, while the section 110 spiral is prevented from moving, section 112 is extended from its length in FIG. 1B to its length in FIG. 1C in response to the hollow core of section 112 selectively receiving the working fluid from the hollow core of section 110. Note that extending section 112 causes distal end 102 to move from point B-1 in FIG. 1B to point C-1 in FIG. 1C.

Section 112 extends in response to valve 111-2 being actuated to an open state, while valve 111-1 remains open and valve 111-3 is closed, for example. For example, section 112 extends in response to the pressure of the working fluid received in the hollow core of section 112 from the hollow core of section 110. In some examples, the pressure of the working fluid received in the hollow core of section 112 might be greater than the pressure of the working fluid received in the hollow core of section 110. For example, the pressure of the working fluid in the hollow core of the section 110 spiral in FIG. 1B might be increased until valve 111-2 opens at which point the working fluid flows into the hollow core of section 112, causing section 112 to extend, as shown in FIG. 1C.

In FIG. 1D, while the section 110 spiral is prevented from moving and segment 112 is extended, section 114 is transformed from its shape in FIG. 1C to the section 114 spiral in response to the hollow core of section 114 selectively receiving the fluid from the hollow core of section 112 so that the section 114 spiral exerts a force on bounding surface 138 sufficient to prevent the section 114 spiral from moving. For examples involving burrowing through the medium, the section 114 spiral might extend into the surrounding medium to prevent the section 114 spiral from moving. In the examples where a fluid, such as blood, might be flowing through opening 130, the section 114 spiral allows the fluid to flow past the exterior of the section 114 spiral, e.g., though the center of the coils of the section 114 spiral, without stopping the flow of the fluid.

Section 114 is transformed from its shape in FIG. 1C to the section 114 spiral in response to valve 111-3 being actuated to an open state while valves 111-1 and 111-2 are open, for example. Note, for example, that the transformation of section 114 into the section 114 spiral can cause section 114 to extend to a length that is greater than the length of section 114 in FIG. 1C, thereby causing distal end 102 to move from point C-1 in FIG. 1C to point D in FIG. 1D. For example, section 114 might extend while section 114 is being transformed into the section 114 spiral.

In some examples, the pressure of the fluid received in the hollow core of section 114 might be greater than the pressure of the fluid received in the hollow core of section 112. For example, the pressure of the working fluid in the hollow core of section 112 in FIG. 1C might be increased until valve 111-3 opens at which point the working fluid flows into the hollow core of section 114, causing section 114 to transform into the section 114 spiral.

Figure 1E:
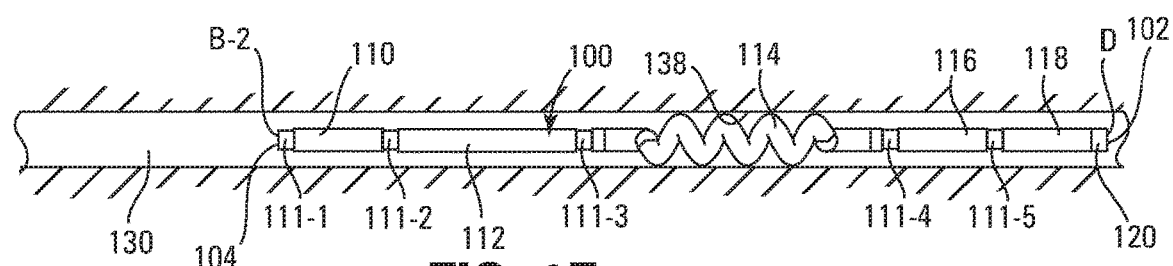

In FIG. 1E, section 110 is returned to its initial, non-spiral shape of FIG. 1A while the section 114 spiral is prevented from moving and section 112 remains extended. For example, section 110 contracts when it is returned to its initial shape, causing proximal end 104 to move from point A-2 in FIG. 1D to point B-2 in FIG. 1E while distal end 102 remains at point D.

For example, section 110 might return to its initial shape in response closing valve 111-2 and reducing the pressure of the fluid in the hollow core of section 110 until section 110 returns to its initial shape while valve 111-1 is kept open.

Figure 1F:
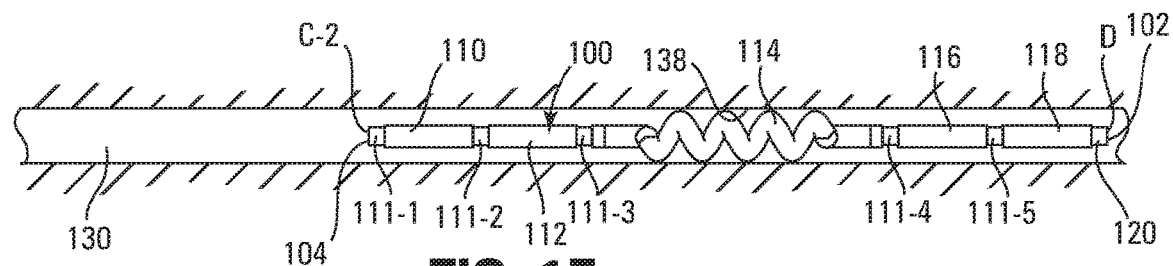

In FIG. 1F, section 112 is contracted to its initial, non-extended length, in FIGS. 1A and 1B while the section 114 spiral is prevented from moving and section 110 remains as in FIG. 1E. Contracting section 112 causes proximal end 104 to move from point B-2 in FIG. 1E to point C-2 in FIG. 1F while distal end remains at point D.

For example, section 112 might contract in response to closing valve 111-3 and reducing the pressure of the fluid in the hollow cores of sections 110 and 112 until section 112 contracts to its initial length while valves 111-1 and 111-2 are kept open.

Figure 4:
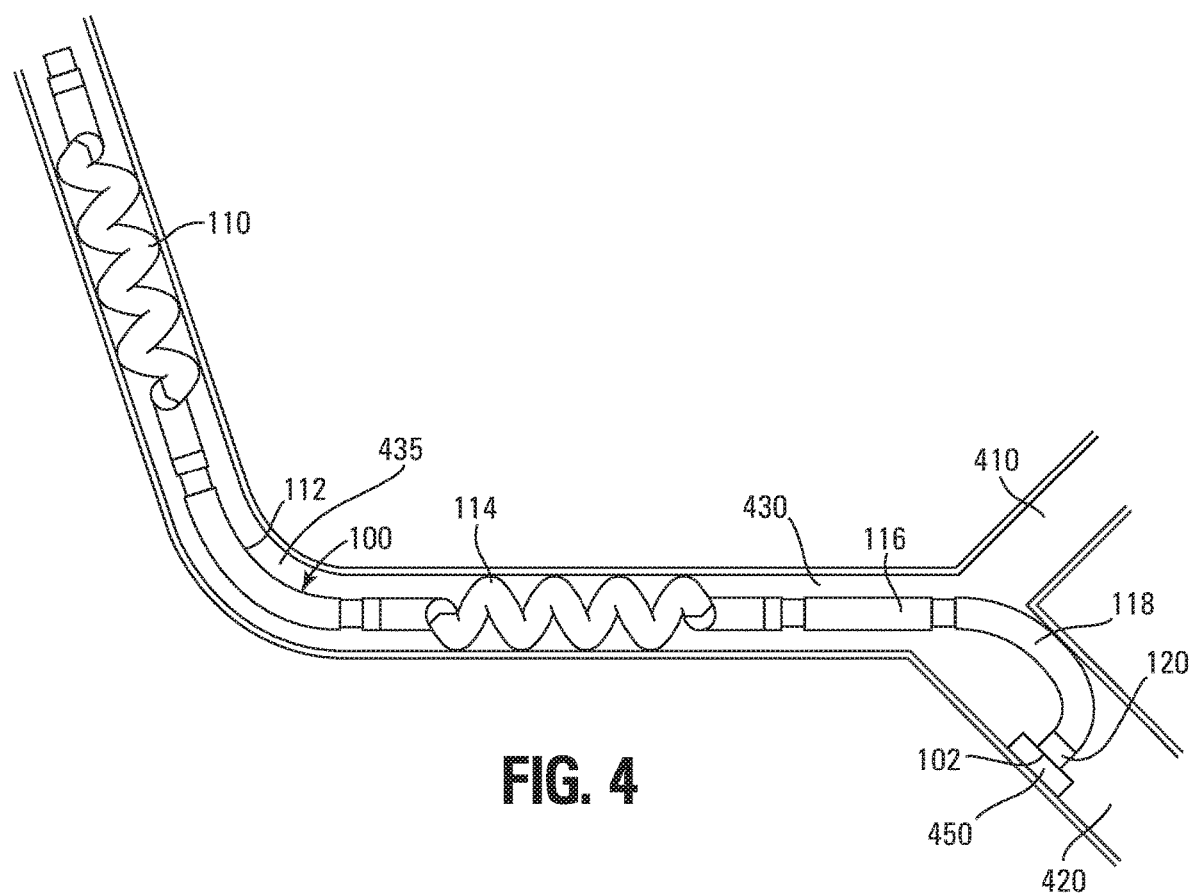
FIG. 4 is an example illustrating a robot moving through an opening.

In some examples, section 120 might include a camera that allows robot 100 to identify branches 410 and 420 in an opening 430, e.g., an opening in an artery, as shown in FIG. 4. This allows an operator to select which of the branches, branch 410 or branch 420, such as branch 420, to enter. For example, the configuration in FIG. 4 is the configuration of FIG. 1D in the opening 430 that has a bend 435 and the branches 410 and 420. Note that FIG. 4 shows that section 112 can be extended through the bend 435.

In some examples, section 118 might be bent from its straight configuration in the configuration of FIG. 1C in response to the hollow core of section 118 selectively receiving the fluid from the hollow core of section 112 through the hollow cores of sections 114 and 116. For example, section 118 might be bent in response to valves 111-3 to 111-5 being actuated to an open state while valves 111-1 and 111-2 are open. For example, the pressure of the fluid received in the hollow core of section 118 might be greater than, but could be less than, the pressure received in the hollow core of section 112, e.g., that causes section 112 to extend. In some examples, section 118 might be configured to bend as robot 100 goes from the configuration in FIG. 1C, while residing in opening 430, to the configuration shown in FIG. 4. Distal end 102, and thus section 120, may be brought into contact with a target material 450, e.g., that may or may not be distinct from the bounding wall of branch 420 of opening 430, for example, using the bending feature of section 118 or using the bending feature of section 118 in combination with the twisting feature of section 116, for example. That is, for example, section 120 may sense target material 450, such as plaque, and/or might remove target material 450.

Figure 5:
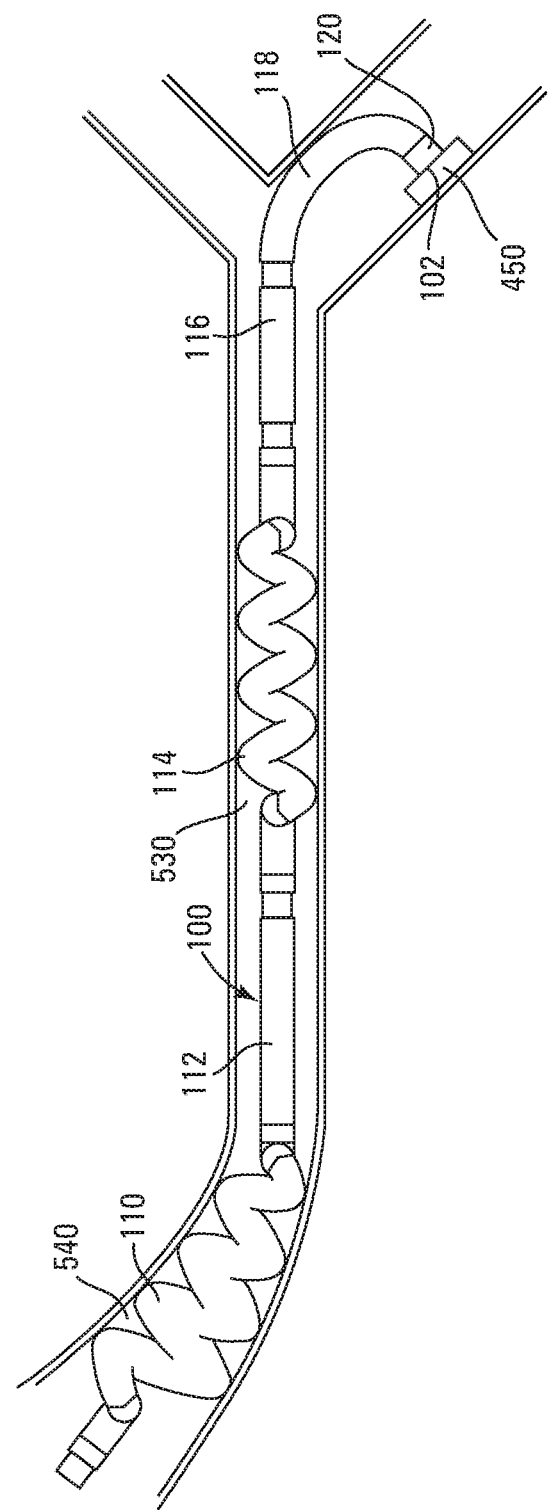
FIG. 5 is another example illustrating a robot moving through an opening.

FIG. 5 shows robot 100 in an opening 530, e.g., of an artery. Opening 530 has a tapered bend 540, and FIG. 5 shows the section 110 spiral conforming to the tapered bend 540. For example, section 110 might be transformed into the section 110 spiral, as described in conjunction with FIG. 1B, while in tapered bend 540. Note that FIG. 5 shows distal end 102, and thus section 120, being brought into contact with target material 450, e.g., using the bending feature of section 118 or using the bending feature of section 118 in combination with the twisting feature of section 116.

Figure 6:
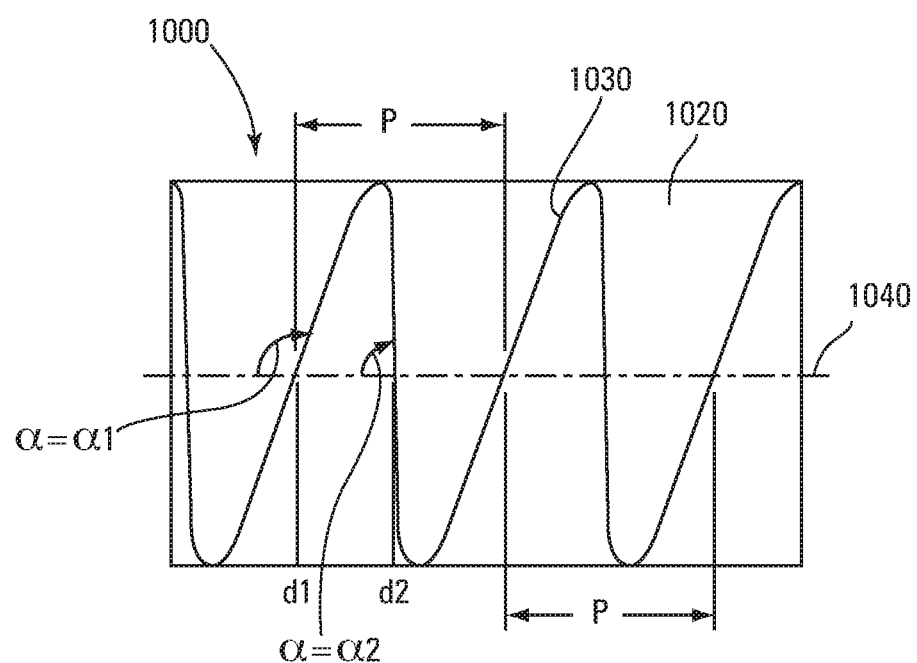
FIG. 6 illustrates an example of a tube that includes a structure that has an angle that varies with distance along the length of the tube.

FIG. 6 illustrates a section or actuator 1000. Section 1000 may be a circular tube having a hollow core, for example. For example, section 1000 may include an elastomeric (e.g., a silicone, rubber, latex, etc.) tube 1020 that includes a structure 1030. In some examples, structure 1030 might be a fiber (a nylon, a woven carbon fiber, etc.), a thickness (e.g., a rib) of an elastomer (e.g., a silicone, rubber, latex, etc.), etc.

For example, an elastomeric rib causes the wall of tube 1020, and thus the wall of section 1000, to be thicker in locations where the elastomeric rib is located. As such, the thickness of the wall of section 1000 will vary. The stiffness of section 1000 will vary accordingly with the thickness of the wall of section 1000 to produce a local anisotropic stiffness distribution in section 1000.

Alternatively, the structure 1030 might be a groove formed by removing a portion of the wall of tube 1020. As such, the wall of tube 1020, and thus the wall of section 1000, will be thinner in locations where the groove is located, meaning that the stiffness of section 1000 will again vary, due to the variation in the thickness of the wall of section 1000, to produce a local anisotropic stiffness distribution in section 1000.

The structure 1030 has a pitch P, as shown in FIG. 6. The structure 1030 makes an angle $\alpha$, measured clockwise from the central axis 1040 of section 1000 that varies with distance along the length of section 1000, and thus along the length of the central axis 1040. For example, the angle $\alpha$ might be an angle $\alpha 1$ at a distance d1 along the length of the central axis 1040 and a different angle $\alpha 2$ at a distance d2 along the length of the central axis 1040. For example, the angle $\alpha$ varies over the pitch P.

The local anisotropic stiffness distribution in section 1000 can be changed by causing the angle $\alpha$ to vary differently along the length of section 1000. For example, the variation of the angle $\alpha$ along the length of section 1000 can be respectively varied to respectively give respective local anisotropic stiffness distributions that respectively allow section 1000 to respectively become the sections 110, 112, 114, 116, and 118 of robot 100. For example, the variation of the angle $\alpha$ along the length of section 1000 might be selected to produce a local anisotropic stiffness distribution that allows section 1000 to become a spiral in response to a fluid pressure in the hollow core of section 1000, to produce a local anisotropic stiffness distribution that allows section 1000 to extend in response to a fluid pressure in the hollow core of section 1000, to produce a local anisotropic stiffness distribution that allows section 1000 to twist in response to a fluid pressure in the hollow core of section 1000, or to produce a local anisotropic stiffness distribution that allows section 1000 to bend in response to a fluid pressure in the hollow core of section 1000.

Figure 7:
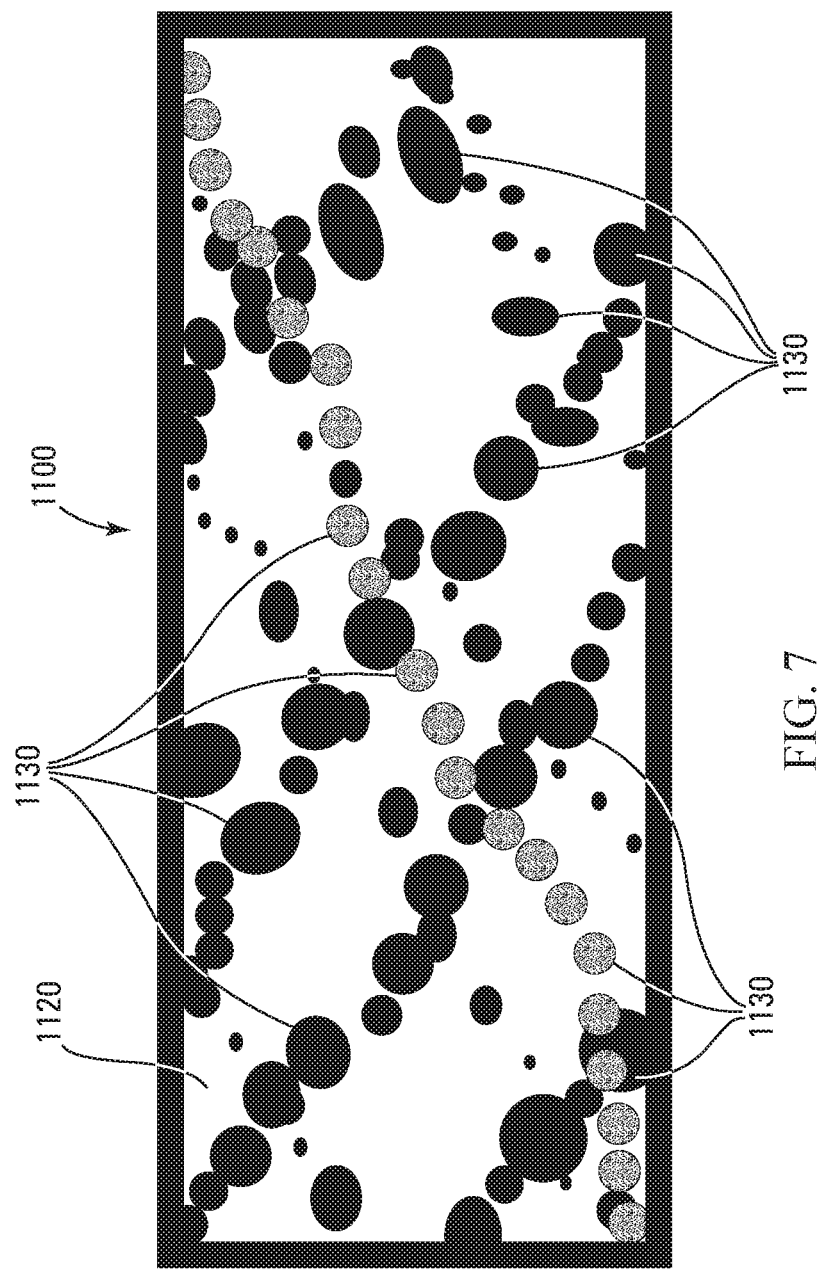
FIG. 7 illustrates an example of a stiffness distribution that allows a tube to be transformed into a spiral in response to an internal pressure.

FIG. 7 illustrates a section or actuator 1100 that can be used for sections 110 and 114 of robot 100. Section 1100 may be a circular tube having a hollow core, for example. Section 1100, for example, may include an elastomeric (e.g., a silicone, rubber, latex, etc.) tube 1120 that includes a structure represented by the distribution of dots 1130. The dots 1130 represent discrete portions that have a different stiffness than tube 1120 where there are no dots 1130 so that section 1100 has a local anisotropic stiffness distribution.

Figure 11:
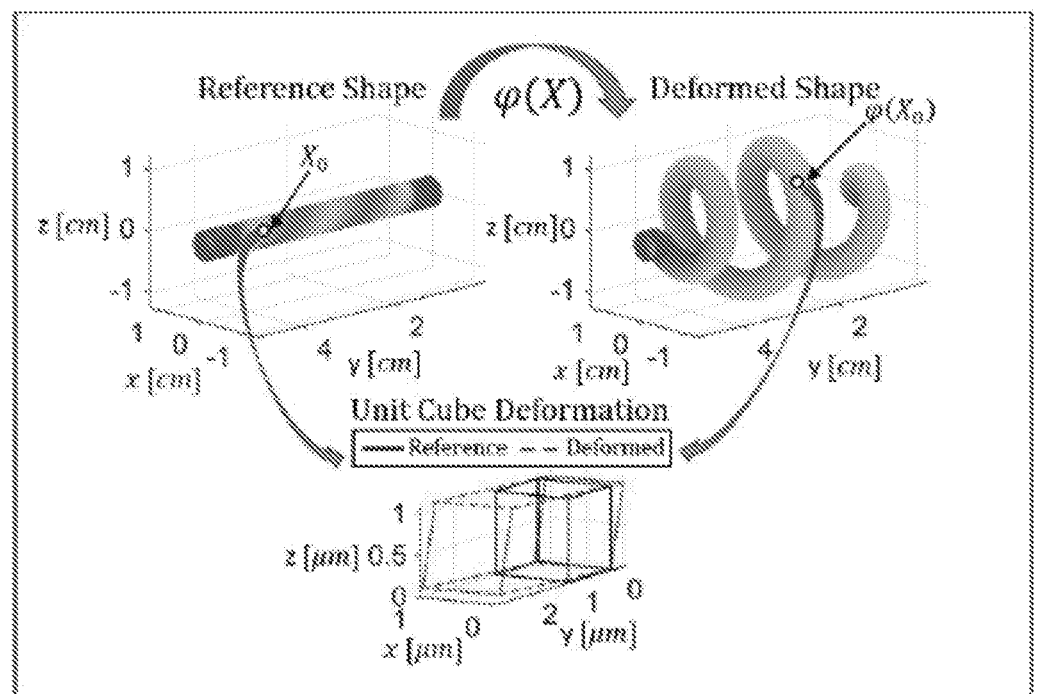
FIG. 11 illustrates an overview of a mathematical approach to designing a material-mapped actuator in accordance with principles of the present disclosure.

For example, dots 1130 might correspond to discrete locations where the wall of tube 1120 might be thicker or thinner than the thickness of the wall of tube 1120 where there are no dots. Alternatively, discrete portions represented by dots 1130 might be of a material (e.g., that might be formed in the wall of tube 1120, such as by molding, three-dimensional printing, etc.) having a different stiffness than the wall of tube 1120 where there are no dots 1130. In the example of FIG. 11, the local anisotropic stiffness distribution may allow section 1100 to become a spiral in response to a fluid pressure in the hollow core of section 1100, meaning that section 1100 can be used for sections 110 and 114 of robot 100.

Figure 8:
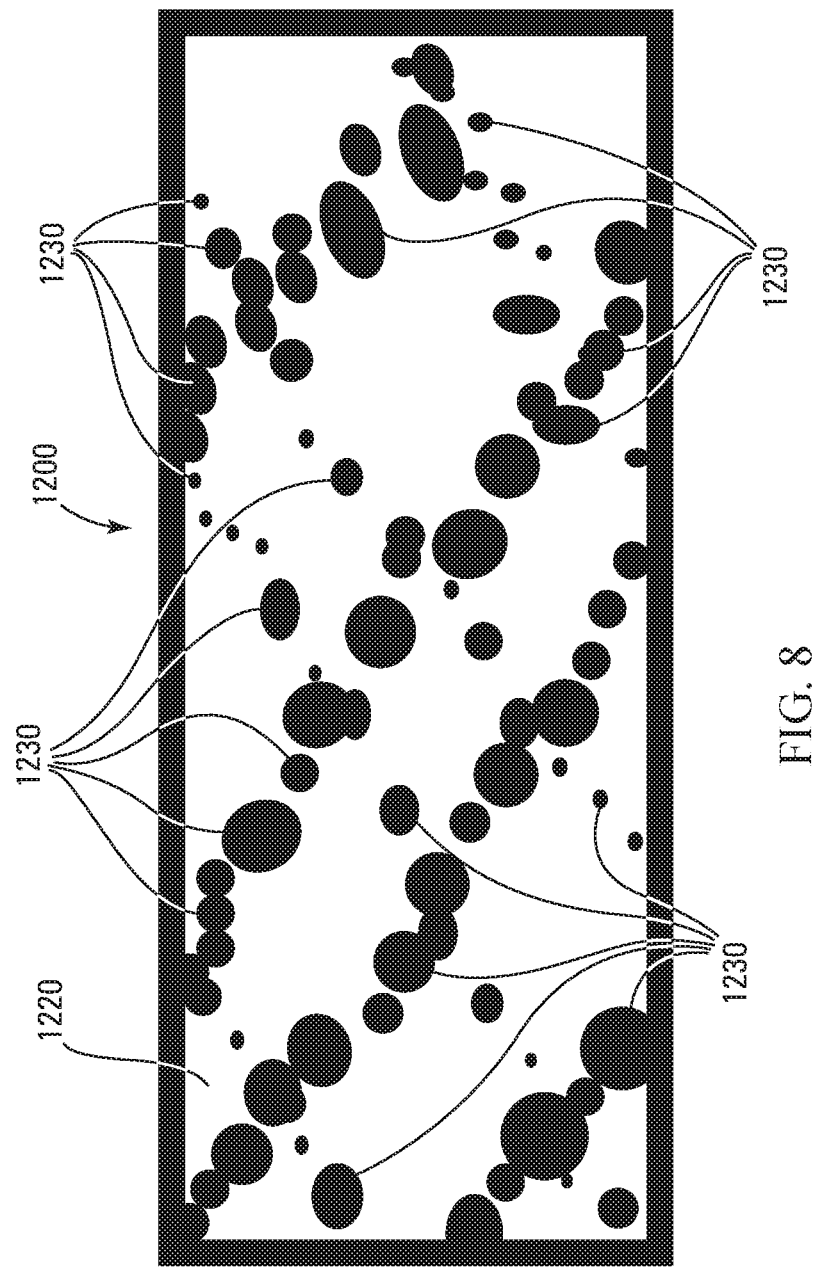
FIG. 8 illustrates an example a stiffness distribution that allows a tube to extend in response to an internal pressure.

FIG. 8 illustrates a section or actuator 1200 that can be used for section 112 of robot 100. Section 1200 may be a circular tube having a hollow core, for example. For example, section 1200 may include an elastomeric (e.g., a silicone, rubber, latex, etc.) tube 1220 that includes a structure represented by the distribution of dots 1230. The dots 1230 represent discrete portions that have a different stiffness than tube 1220 where there are no dots 1230 so that section 1200 has a local anisotropic stiffness distribution.

Figure 12:
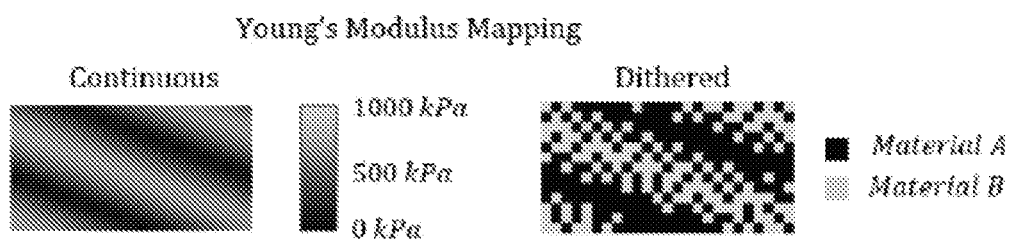
FIG. 12 represents conversion of material mapping information to manufacturing blueprint information using a dithering algorithm in accordance with principles of the present disclosure.

For example, dots 1230 might correspond to discrete locations where the wall of tube 1220 might be thicker or thinner than the thickness of the wall of tube 1220 where there are no dots. Alternatively, discrete portions represented by dots 1230 might be of a material (e.g., that might be formed in the wall of tube 1220, such as by molding, three-dimensional printing, etc.) having a different stiffness than the wall of tube 1220 where there are no dots 1230. In the example of FIG. 12, the local anisotropic stiffness distribution may allow section 1200 to extend in response to a fluid pressure in the hollow core of section 1200, meaning that section 1200 can be used for section 112 of robot 100.

Figure 9:
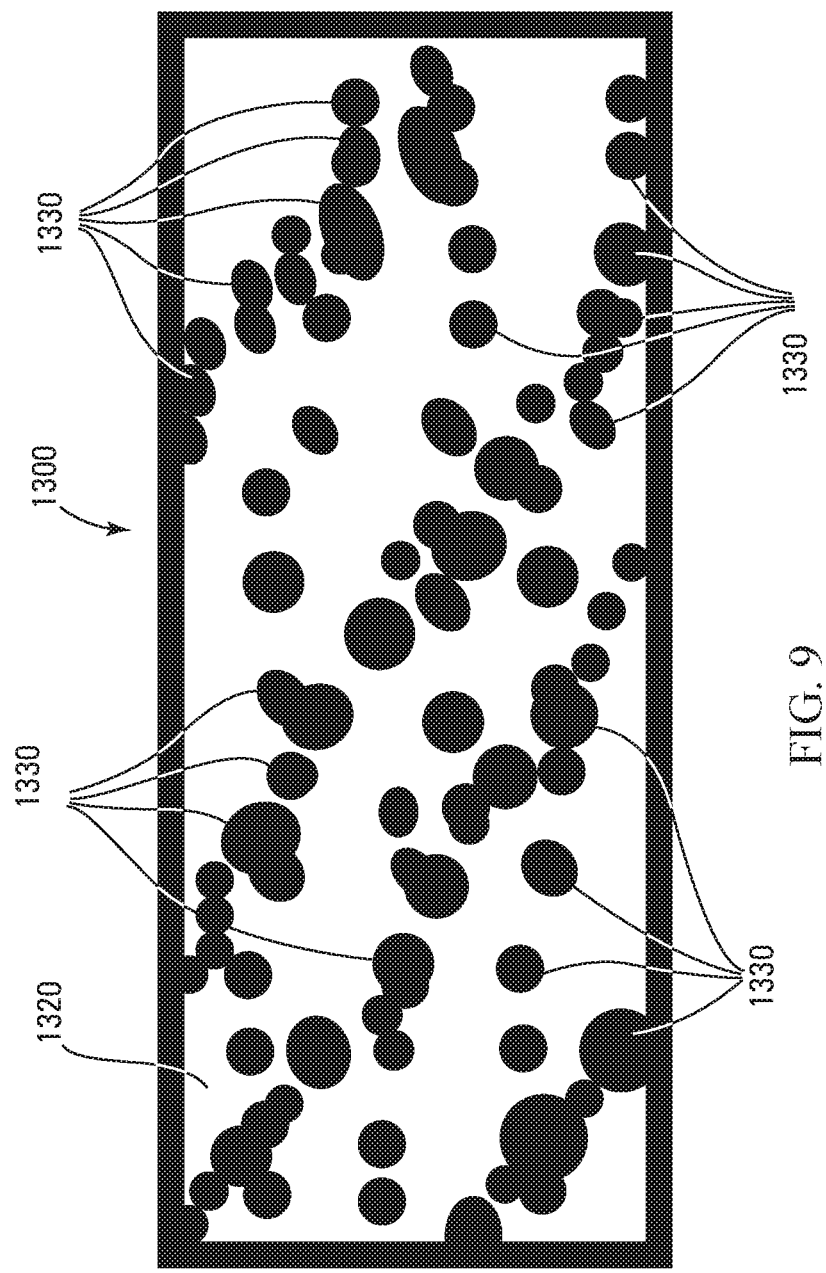
FIG. 9 illustrates an example a stiffness distribution that allows a tube to twist in response to an internal pressure.

FIG. 9 illustrates a section or actuator 1300 that can be used for section 116 of robot 100. Section 1300 may be a circular tube having a hollow core, for example. For example, section 1300 may include an elastomeric (e.g., a silicone, rubber, latex, etc.) tube 1320 that includes a structure represented by the distribution of dots 1330. The dots 1330 represent discrete portions that have a different stiffness than tube 1320 where there are no dots 1330 so that section 1300 has a local anisotropic stiffness distribution.

Figure 13:
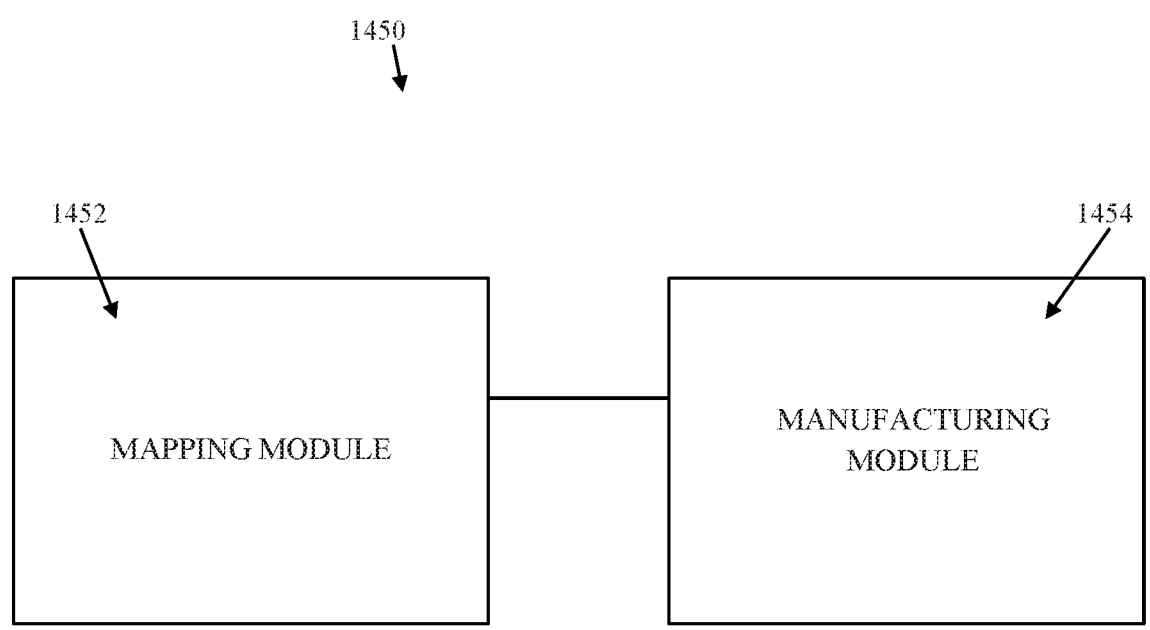
FIG. 13 is a schematic illustration of a system for manufacturing a soft robot in accordance with principles of the present disclosure.

For example, dots 1330 might correspond to discrete locations where the wall of tube 1320 might be thicker or thinner than the thickness of the wall of tube 1320 where there are no dots 1330. Alternatively, discrete portions represented by dots 1330 might be of a material (e.g., that might be formed in the wall of tube 1320, such as by molding, three-dimensional printing, etc.) having a different stiffness than the wall of tube 1320 where there are no dots 1330. In the example of FIG. 13, the local anisotropic stiffness distribution may allow section 1300 to twist in response to a fluid pressure in the hollow core of section 1300, meaning that section 1300 can be used for section 116 of robot 100.

Figure 10:
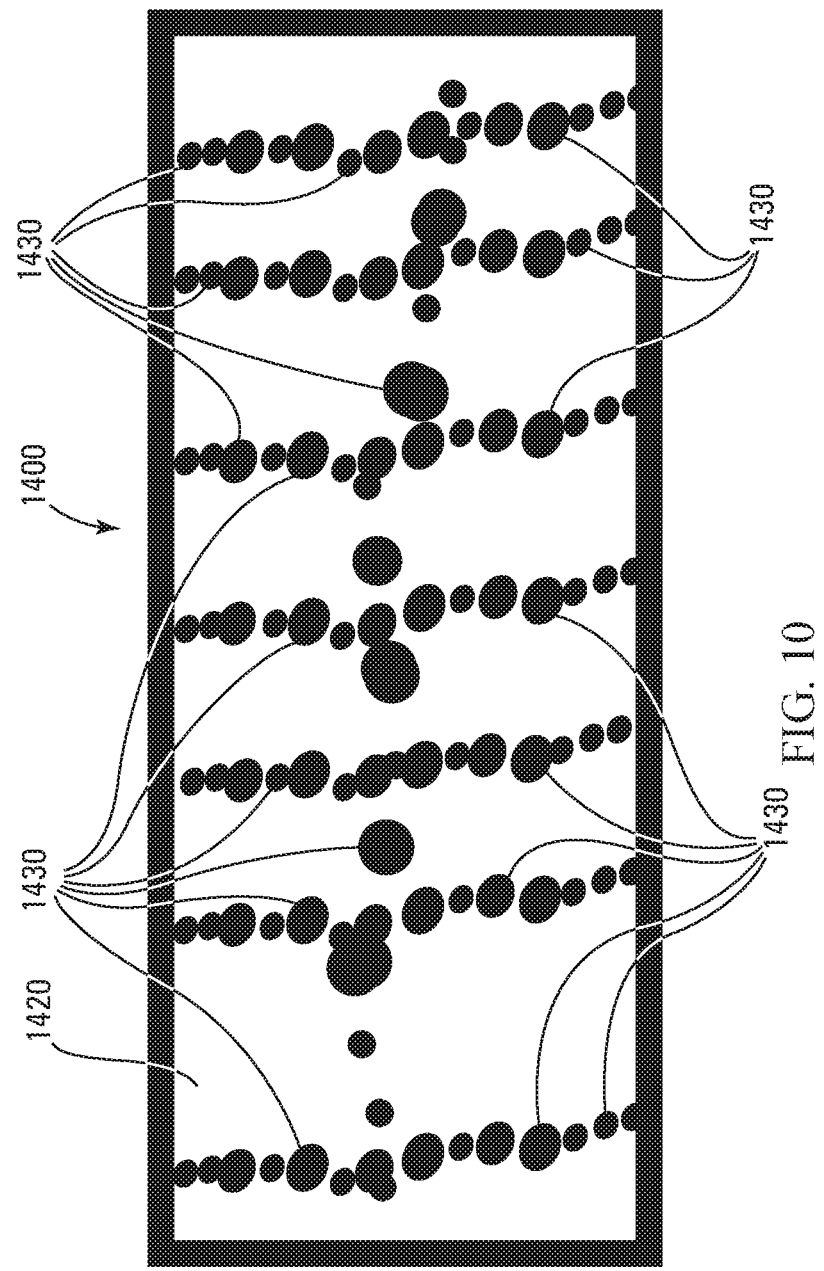
FIG. 10 illustrates an example a stiffness distribution that allows a tube to bend in response to an internal pressure.

FIG. 10 illustrates a section or actuator 1400 that can be used for section 118 of robot 100. Section 1400 may be a circular tube having a hollow core, for example. For example, section 1400 may include an elastomeric (e.g., a silicone, rubber, latex, etc.) tube 1420 that includes a structure represented by the distribution of dots 1430. The dots 1430 represent discrete portions that have a different stiffness than tube 1420 where there are no dots 1430 so that section 1400 has a local anisotropic stiffness distribution.

For example, dots 1430 might correspond to discrete locations where the wall of tube 1420 might be thicker or thinner than the thickness of the wall of tube 1420 where there are no dots. Alternatively, discrete portions represented by dots 1430 might be of a material (e.g., that might be formed in the wall of tube 1420, such as by molding, three-dimensional printing, etc.) having a different stiffness than the wall of tube 1420 where there are no dots 1430. In the example of FIG. 10, the local anisotropic stiffness distribution may allow section 1400 to bend in response to a fluid pressure in the hollow core of section 1400, meaning that section 1400 can be used for section 118 of robot 100.

Actuators 1000 (FIG. 6), 1100 (FIG. 7), 1200 (FIG. 8), 1300 (FIG. 9), 1400 (FIG. 10) described above are non-limiting examples of actuators with mechanical properties that spatially vary along the actuator body coordinate system in accordance with some embodiments of the present disclosure. With this in mind, some aspects of the present disclosure relate to methods of designing and manufacturing one or more actuators having mechanical properties that spatially vary along the actuator body useful as or with a soft robot and mapped to performance parameters entailed or required by a particular end-use application. These constructions can be referred to as a "material-mapped actuator". As a point of reference, many envisioned soft robot end-use applications will require the soft robot to transition or articulate through multiple different shapes, elongations, point stiffnesses, etc. throughout the procedure. Material-mapped actuators can be uniquely designed and manufactured in accordance with methods of the present disclosure to satisfy essentially any end-use design constraint, including achieving desired, differing shapes (or stiffness or other property such as applying a force on to an external body or object) throughout the end-use procedure.

In general terms, the material-mapped actuators of the present disclosure are premised upon the actuator designs described above in which a material (e.g., any of the "dots" described above) is applied to or in an elastomeric tubular body or hollow core. A discernible or macro shape associated with the material-mapped actuator is primarily generated by the tubular body. In the presence of a fluid medium (or "actuation medium") passing through the tubular body, a property (e.g., shape, elongation, stiffness, etc.) of the tubular body (and thus of the material-mapped actuator as a whole) is caused to change as a function of the applied material. With this in mind, the material-mapped actuator is formed to provide an initial shape having a corresponding initial map of mechanical attributes consisting of locally-varying stiffness at each point in a volume of the tubular body. The material-mapped actuator is further configured such that in the presence of a fluid medium distributed within the tubular body, the material-mapped actuator changes to a new, different shape or different distribution of mechanical properties with the initial spatially-varying map of mechanical attributes influencing or dictating the new shape or distribution.

In some embodiments, the material-mapped actuator consists of an elastomer or combination of elastomers (either by locally continuous mixtures or locally discrete combinations) such that local mechanical properties (e.g., stiffness) are specified and possibly distinct at each point in the actuator body. In other embodiments, the material-mapped actuators of the present disclosure includes or consists of an elastomeric tube or other shape, or is constructed on top of an elastomeric tube (or other shape). In yet other embodiment material-mapped actuators of the present disclosure, the material applied to the elastomeric tubular body includes local, spatially-varying additives such as locally-oriented fibers, meshes, threads, fiberglass, carbon black or carbon fiber, knits, woven materials, or similar materials that induce desired material anisotropies and strain limiting behaviors where the fiber orientation or pitch is free to vary in any direction along the actuator body. That is to say, the applied fibers (or other shaped material) need not extend an entire length of the tubular body and need not exhibit a constant pitch (e.g., can be akin to chopped fibers or small meshes applied and oriented locally). In related embodiments, the fiber- or mesh-like materials can be pre-stretched, pre-compressed, or pre-bunched prior to application to the tubular body so as to influence different regions of the local material stress-strain curve (e.g., have little effect on mechanical properties during small stretches (or elongations) and begin to have a dominant effect at higher stretches).

Commensurate with the descriptions above, the material-mapped actuators of the present disclosure provide or define one or more cavities (e.g. flow passage(s) described above) that accepts an actuation media (e.g., fluid medium). The actuation media can be a changing volume fluid (i.e., liquid or gas), such as water, oil, air, etc., which fills the cavity (or cavities) with this change in volume effecting a change in the shape of the material-mapped actuator and/or change in spatial distribution of mechanical properties. In some embodiments, the material-mapped actuator is configured such that the work done by the actuation media induces a stretching force along a surface of the material-mapped actuator and the spatially varying stiffness induces a desired (or pre-determined) change in the overall shape of, and/or in external forces generated by, the material-mapped actuator.

In other embodiments, a property mapped into the material-mapped actuator is different than or includes attributes other than material stiffness. For example, local volumes of active materials that grow or shrink in size in spatially-dependent magnitudes due to an applied stimulus such as electric, magnetic, electromagnetic, thermal, mechano-vibrational, acoustic or optic stimuli (e.g., made of electro-active polymers or thermally- or electrically-responsive hydrogels) can be specified. With these optional mapping techniques, the combination of local growth from multiple sites can result in a desired final body shape or external force application.

In other embodiments, the local, spatially-varying mechanical properties of the material-mapped actuators of the present disclosure depend on time and/or stress. With this in mind, the material-mapped actuator can be configured such that the time and/or stress dependent properties influence the overall sequence or evolution of the shape of the actuator body over time and/or stress. For example, with embodiments in which the tubular body of the material-mapped actuator is hyperelastic, the material-mapped actuator can be configured to exploit non-linear hyperelastic characteristics such as nonlinearity, hysteresis, memory, and non-monotonic stress-strain curves to better ensure that actuation begins at lower pressures in less than all of the actuator (e.g., only one part or segment of the actuator is actuated or experiences a change at a lower pressure).

In yet other embodiments, the material-mapped actuator is configured such that the local spatially-varying mechanical properties (e.g., stiffness) change in response to an external stimulus (e.g., glass transition due to applied temperature, change in viscoelastic properties due to vibration in the medium, non-Newtonian characteristics of material such as a shear-thickening elastomer). With these optional constructions, a single material-mapped actuator can be configured to assume a plurality of different orientations for a given activation of the actuation medium based on the stimulus.

In yet other embodiments, the material-mapped actuator is configured such that the local material stiffness in each location of the actuator body is, at least in part, determined or dictated by the local thickness of the material.

By incorporating one or more or all of the above local spatially-varying mechanical properties, the material-mapped actuators of the present disclosure can be configured to assume multiple desired shapes in the presence of an applied actuation medium. With these constructions, the material-mapped actuator can be uniquely configured to exhibit a pre-determined actuation sequence from an initial state (e.g., shape) to a first final state having at least one property (e.g., shape) differing from that of the initial state and corresponding with a desired attribute of the end-use procedure; the first final state then because a "new" initial state for subsequent actuation to a new, second final state having at least one property (e.g., shape) differing from that of the first final state, etc. Thus, a single material-mapped actuator of the present disclosure can be configured to achieve a plurality (e.g., three or more) of different, desired shapes as part of the actuation sequence. Notably, while example actuators have been described as including a tubular actuator body, the material-mapped actuators and corresponding methods of mapping, designing and manufacturing of the present disclosure are in no way limited to tubular shape. The techniques of the present disclosure can be utilized with virtually any initial shape, including spherical, planar, amorphous, etc.

The performance or operational characteristics incorporated into the material-mapped actuators can be determined in various fashions. In some embodiments, methods of the present disclosure apply continuum mechanics (e.g., deformation mapping, deformation gradients, stress-strain tensors, etc.) as part of an inverse design technique. Inverse design is in reference to generalizable computational methods that map directly from arbitrary task requirements to the optimal design of more universal soft robots and actuators and mechanisms, independent of the actual manufacturing techniques employed. For a particular soft robot end-use application, task or procedure, at least a desired initial state or shape and final state or shape (or other performance parameter, such as exertion of force on an external body or object) of the soft robot will be known or can be determined. In many instances, one or more desired, intermediate, procedure-specific states or shapes will also be known or can be determined. This information, in turn, is utilized to provide an optimal mapping of elasticity and materials to construct a soft robot (including one or more material-mapped actuators) well-suited to perform the identified end-use application or procedure, conforming to the procedure-required states or shapes when fluid power (or other actuation medium) is applied.

The inverse design methods can be embodied by a computer "toolbox" (continuum deformation mappings) employed as part of a system for manufacturing a soft robot (and/or one or more material-mapped actuators to be used with a soft robot). The systems of the present disclosure can include a computing device including one or more processors and a memory as known in the art. The computing device incorporates the inverse design toolbox as processing software, optionally stored in the memory, configured to receive information indicative of one or more end-use application performance requirements and/or kinematic constraints, such as desired initial shape, final shape, and optionally one or more intermediate shapes, and generate optimal mapping of elasticity and materials for constructing the soft robot (or individual material-mapped actuator(s) thereof). The computing device can further be electronically connected to (or provided as part of) a machine adapted to form a material-mapped actuator based upon, or dictated by, information generated by the inverse design toolbox as described in greater detail below, using a generated digital "blueprint" that informs of the best choice of manufacturing techniques.

The inverse design toolbox can include or operate on a mathematical formulism that precisely describes the continuum displacements, and in some embodiments is sufficiently universal to handle virtually any soft shape. By way of example, a material-mapped actuator formed to generate a spiral shape can be described by continuum mechanics equations as generally reflected by FIG. 11 (that otherwise shows a tubular actuator of the present disclosure in an initial or reference shape and in a deformed shape (spiral)). The equations below represent one non-limiting example of a description of the mechanics of the motion in accordance with principles of the present disclosure. First, a parametric curve, r(t), is used to define the "spine" of each segment of the deformed shape whose dimensions are directly dictated by the task or procedure to be performed. An envelope function, $f_{env}(\cdot)$, can be applied to ensure the ends of the spiral line up with its axis and connect smoothing with adjacent segments to result in the desired shape. This approach can generalize traditional robotic concepts such as generalized joint angles q for rigid body transforms (e.g., in DH parameters), for example, L for actuator length (traditional prismatic joint extension) and R for spiral expansion (not available in traditional robotics) and q={L, R}. Both can be dictated by procedure specific geometry. Analytical forms for the tangent T(t), normal N(t), and binormal B(t) vectors dictated by classic Frenet-Serret geometry can be derived from $r_{spine}$ as:

$$T(t)=r'(t)/\|r'(t)\|;$$

$$N(t)=T'(t)/\|T'(t)\|;$$

B(t)=T(t)×N(t) provided that it is twice differentiable.

This demonstrates that a universal actuator design can be generated by a curve fitting method like cubic splines instead of synthesized a priori from analytical functions. Thus, the inverse design toolbox and corresponding methods of the present disclosure can operate on empirical data constraints. Optionally, additional variables can be implemented that parameterize a desired surface along $r_{spine}(\ )$ for the soft robot body. For example, a cylindrical surface, $S_{spiral}(\ )$, extended axially by t about $r_{spine}(\ )$ and wrapped radially by Θ can have a radius $R_i$ dictated by the end-use application task or procedure (e.g., not more than 1 cm diameter). That is, $S_{spiral}(\Theta, t, R, R_i, f_{env})=r_{spine}(t)+R_i(N(t)\cos(\Theta)+B(t)\sin(\Theta))$. This allows $S_{spine}(\ )$ to fully describe the desired kinematics of this link, starting from a straight cylinder and ending in a spiral with no twist or change in length (attributes not possible with existing soft robot design methods).

The inventors of the present disclosure have observed that the $S_{spiral}(\ )$ derived for soft actuators as above is equivalent to a deformation mapping $\varphi(\cdot)$ in continuum mechanics, commonly denoted as $x=\varphi(X)$ where X=[X Y Z] and x=[x y z] correspond to undeformed and deformed shapes, respectively. If $\varphi(\cdot)=S_{spiral}(\cdot)$, the tools of continuum mechanics can be invoked to describe soft robot kinematics. For example, the deformation gradient:

$$F = \frac{\partial \varphi(X)}{\partial X}$$

leads to the right Cauchy Deformation Gradient:

$$C = F^T F$$

which can yield the stress tensors calculated as:

$$\lambda_i = \sqrt{C_{ii}}, \ i = 1, 2, 3$$

The diagnolization of $\lambda$ is:

$$\lambda = \begin{bmatrix} \lambda_1 & 0 & 0 \\ 0 & \lambda_2 & 0 \\ 0 & 0 & \lambda_3 \end{bmatrix}$$

The angle of deformation can be expressed via the Polara Decomposition of $C_{ij}$ or alternatively as:

$$\theta_{ij} = \mathrm{acos}\left(\frac{C_{ij}}{\lambda_i \lambda_j}\right), \ \begin{array}{l} i = 1, 2, 3 \\ j = 1, 2, 3 \end{array}$$

or $$[\theta_{12} \ \theta_{13} \ \theta_{23}] = \left[\mathrm{acos}\left(\frac{C_{12}}{\lambda_1 \lambda_2}\right) \ \mathrm{acos}\left(\frac{C_{13}}{\lambda_1 \lambda_3}\right) \ \mathrm{acos}\left(\frac{C_{23}}{\lambda_2 \lambda_3}\right)\right]$$

This produces 3×3 symmetric matrices, where the diagonals are all 0 and can be reduced down to three rotations. The above observations allow the methods of the present disclosure to take any point $X_0$ on the initial (reference) shape and analyze the local anisotropic deformation. For example, a point $X_0$ can be selected in the reference shape and a unit cube can be plotted to show the reference and deformed cube configuration as:

$$P_{cube\ deformed} = \lambda R_{ZYX} P_{cube\ reference}$$

$R_{ZYX}$ can be represented by the Euler Angle Rotation $\Theta_{12}$, $\Theta_{13}$, $\Theta_{23}$ as:

$$R_{ZYX} = R_Z(\Theta_{12}) R_Y(\Theta_{13}) R_X(\Theta_{23})$$

The above methodology or process is shown graphically in FIG. 12. It will be recognized that significant anisotropy and elongation of nearly 300% is considered. This map provides the required material stiffness at each point on the actuator's ski required to make the actuator (and thus the resultant soft robot) move from an initial shape to a desired shape.

This approach can also account for kinematic forces. An approximation for the peak stress at each point on the "skin" of the actuator is:

$$\dot{E} = \frac{\sigma}{\varepsilon} = \frac{P_{max} r_{max}}{\varepsilon t_h},$$

using circumferential hoop stress of a thin walled cylinder. The maximum internal cavity pressure, $P_{max}$, and maximum desired tube diameter, $r_{max}$, at this pressure can both be selected in accordance with desired performance parameters of the end-use application or procedure. The wall thickness, $t_h$, can be left as a free design variable provided $t_h < R_{max}/10$ to meet hoop equation assumptions. E maps the magnitude of local change in strain required at each point on the surface ($\Theta$, t) to achieve the desired motion. For the non-limiting example spiral actuator, this can range from a 0% to 300% change from strain at rest in some embodiments. Thus, for an approximately linear material in this range (such as Kraton D1161), Hooke's law applies and can yield the magnitude of change in material stiffness required at each point on the surface of the initial shape to achieve the desired shape and meet static pressure and force requirements (e.g., the "blueprint" for manufacturing). Nonlinear materials in this elongation region such as latex may entail a model that is accurate in the regime of large elongation such as Gent models to determine a specific material's stiffness and hence a more accurate "blueprint".

Optionally, the stiffness mapping systems and methods of the present disclosure can apply the Cauchy-Stress tensor so as view stress over multiple planes. It can be possible to solve for the Cauchy-Stress tensor as a function of a material model, but may leave too many unknowns. Instead, internal pressure can be applied as boundary condition that is related to the Cauchy-Stress tensor; this would eliminate a set of unknowns and more easily identify or solve for the material property. The Cauchy-Stress tensor can be broken into hydrostatic stress (pressure) and devatoric stress (shear) as:

$$\sigma = s - pI$$

The hydrostatic pressure can then be solved for material constant $c_1$ as:

$$p = -\frac{1}{3} tr(\sigma)$$

$$c_1 = -\frac{3P}{2I_1 tr(B)} = -\frac{3P}{2 tr(B)^2}$$

This can be performed for each point and a mapping created of the material parameter as a function of position. A dithering algorithm can then be run to reduce the value of $c_1$ to two. The resultant Cauchy-Stress equation can be expressed as:

$$\sigma = 2W_{J_1} F + 2W_{J_2}(I_1 F - B^2) - c_0 I$$

Figure 16:
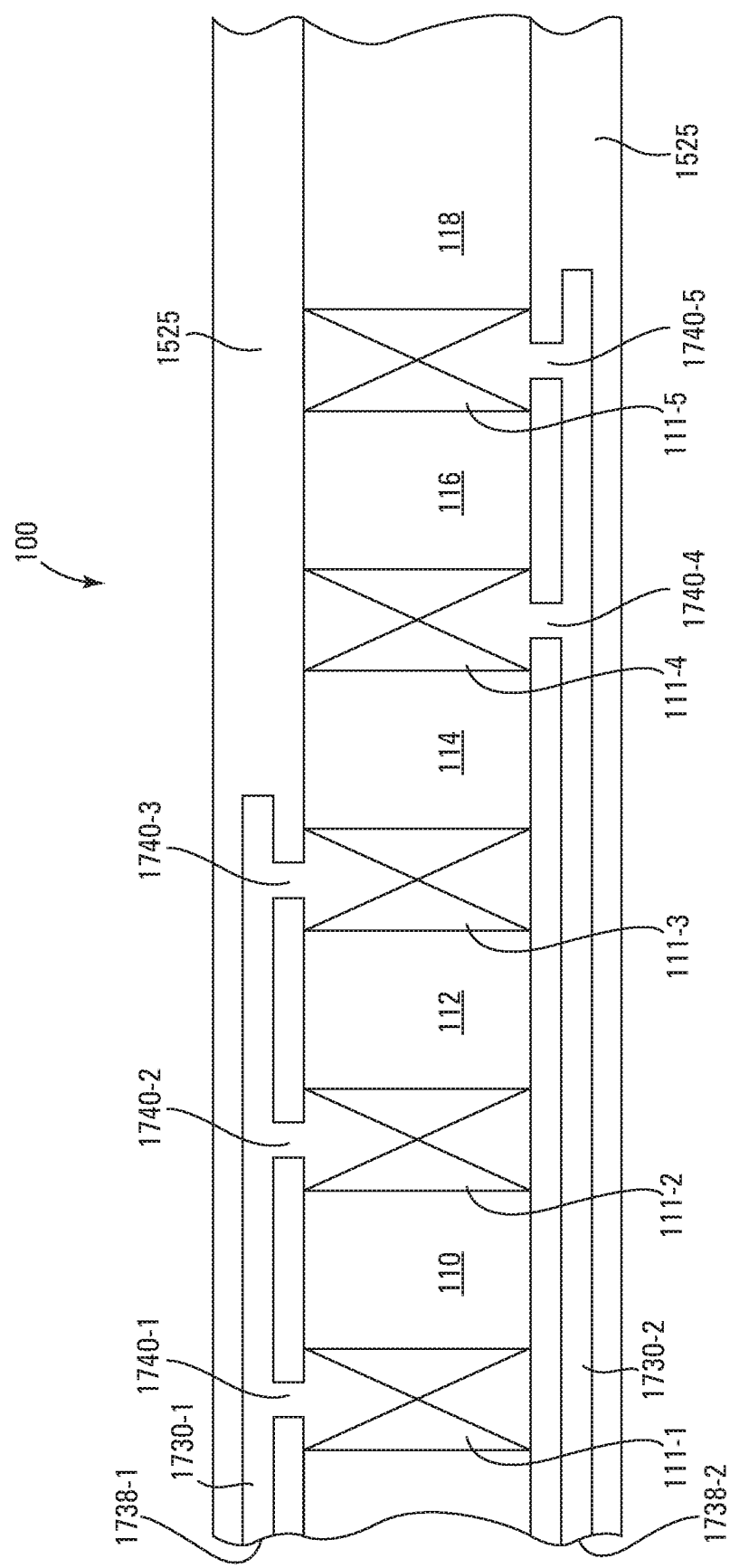
FIG. 16 illustrates an example of a robot having pilot lines at different locations in a wall.

By utilizing the stiffness map, $E(\Theta, t)$ as described above, systems and methods of the present disclosure can provide an optimized blueprint for constructing a corresponding material-mapped actuator. This can allow a free choice of suitable manufacturing methods or, if no ideal methods are available, the blueprint dictates what an optimal manufacturing method should strive to achieve. In some embodiments, a digital manufacturing blueprint is automatically generated based upon the desired stiffness map that otherwise corresponds to one or more shapes implicated by the end-use application or procedure. For example, a discretizing algorithm can be applied to the continuum desired material mapping such that the global effect of the discretized mapping is equivalent to the original continuum desired material mapping. In some embodiments, the discretized mapping entails an algorithm akin to the Floyd-Steinberg dithering algorithm, modified to have error diffusion minimize the global stiffness in error (possibly mapped through nonlinear stress-strain for certain materials such as latex) and implemented to minimize error for multiple anisotropic directions. In one exemplary format, the dithering algorithm accounts for two materials having different Young's modulus. The first material is selected in accordance with the lowest stiffness bound established by the stiffness mapping. The peak stiffness from the stiffness mapping will dictate selection of the second material. For example, the two different materials could be two different durometers of silicone, two different thicknesses of latex, two different durometers of a thermoplastic elastomer, etc. Regardless, the dithering algorithm maps an arrangement of the second material on to the first material in accordance with stiffness mapping. FIG. 16 provides an example of a Young's Modulus mapping provided by the dithering algorithms of the present disclosure required near point $X_0$ to realize desired overall deformation.

Optionally, the discretized algorithm can be a volumetric dithering algorithm capable of discretizing a continuous material property mapping to a desired spatial resolution. In some embodiments, a set of stress maps is created with a single parameter being varied. For example, in the spiral parameterization the helix radius R can be varied and a specific pressure assigned to each radius R. A stress map is created for each iteration of the helix radius and pressure. The set of stress maps is then run through filtering and dithering algorithms to yield a single stress map that is able to actuate through several precision points that are created by each iteration.

Other algorithms can be utilized for formatting or generating the manufacturing blueprint from the stiffness mapping, for example as a function of the machines or equipment available for generating the material-mapped actuator. As a point of reference, FIG. 13 schematically illustrates one embodiment of a system 1450 in accordance with principles of the present disclosure for manufacturing a material-mapped actuator useful as, or as part of, a soft robot configured to perform a desired or pre-determined end-use application, procedure or task. The system 1450 includes a mapping module 1452 and at least one manufacturing module 1454. The mapping module 1452 includes a computing device programmed (or operating on software) to generate a stiffness mapping for a selected end-use application, procedure or task as described above, and to generate a manufacturing blueprint in accordance with the descriptions above. The mapping module 1452 can include one or more user input devices (e.g., touch screen, keyboard, etc.) by which a user can enter or select (e.g., in response to a prompt generated by the mapping module) one or more end-use application, procedure or task parameters. The user-entered or selected parameter(s) can include one or more of desired initial and final (and optionally intermediate) shapes, size, external forces, force applied to an external body, peak pressures, motion, etc. The mapping module 1452 can further be programmed to consider capabilities or techniques embodied by the manufacturing module 1454 in formulating the manufacturing blueprint.

The manufacturing module 1454 can assume a wide variety of forms capable of producing or generating a material-mapped actuator of the present disclosure, operating upon the manufacturing blueprint generated by the mapping module 1452. In other embodiments, the mapping module 1452 can be programmed or configured to generate a stiffness mapping as described above, and the manufacturing module 1454 can include appropriate computing device hardware and/or software for generating an appropriate manufacturing blueprint based upon the stiffness mapping. Regardless, the manufacturing module 1454 includes or comprises one or more machines or devices for forming material-mapped actuator useful as or with a soft robot. For example, the manufacturing module 1454 is configured to be capable of imparting a material-mapping pattern onto or throughout a core body that is either provided to, or formed by, the manufacturing module. The material-mapping pattern can be generated with either an additive or subtractive manufacturing technique.

For example, the manufacturing module 1454 can be or include an additive-type device utilizing one or more of inkjet deposition, aerosol jet deposition, or extrusion deposition (e.g., 3D printer as known in the art). In some embodiments, the deposition process effectuated by the manufacturing module 1454 can be controlled in terms of one or both of the type of material being deposited and the material thickness at specified locations. In some related embodiments, the manufacturing module 1454 can be configured to perform digitally dithered material placement to achieve discrete elastomeric properties and/or durometers across the material-mapped actuator (and/or the resultant soft robot). In other related embodiments, the manufacturing module 1454 can be configured to perform continual mixing of elastomers where the mixing ratio of the base elastomers is varied throughout the deposition process to achieve continuous variation of elastomeric properties or durometers. By way of one non-limiting example, the manufacturing module 1454 can be akin to a CNC lathe with additional mechanical extrusion and piezo-jet nozzles for depositing droplets of high-viscosity elastomer resins with a surface deposition resolution of 0.5 mm or less. This allows printing at higher precision using established materials (e.g., aqueous latex, various silicones) and curing techniques (air dry, thermal vulcanization, UV initiated, mixed catalyst platinum cure, etc.). Moreover, new materials can be printed, such as thermoplastic elastomers that exhibit very high elongation rates (greater than 1000%) but have a more linear stress-strain response than latex.

Another additive manufacturing technique or step can include dip molding, with the manufacturing module 1454 optionally configured to control a material wall thickness of the actuator in response the time each region spends in the dip solution.

Alternatively or in addition, the manufacturing module 1454 can be or include a modified braiding machine, manual, or real-time robotic weaving, sewing or knitting of fibers to integrated into the structure of the material-mapped actuator. With these optional embodiments, pre-tensioning or pre-compression of the fibers during or upon deposition can be provided as desired.

Alternatively, the manufacturing module 1454 can be configured to perform a subtractive manufacturing process. Non-limiting examples include laser ablation, waterjet ablation (aquablation), precision machining, abrasion, etc. In optional, related embodiments, the manufacturing module 1454 can include or operate upon a concentric arrangement of tubular bodies. The tubular bodies can be subtractively manufactured using laser ablation, cutting or dissolution to remove a specified number of tube layers over a programmable region to change the elastomeric properties and/or thickness of the concentric arrangement to achieve desired deformations.

In yet other embodiments, the manufacturing module 1454 can be or include a pick and place-type robot that selects one, or a combination of, pre-assembled stiffness element(s) onto a hollow core. The elements can be combined or overlaid to achieve strain responses not possible with a single fiber. Exemplary stiffness elements include pre-tuned fabric/fiber meshes, mesh patches, chopped or milled fibers, stretchable fibers, pre-tensioned or pre-compressed fiber elements, etc. In related embodiments, long fibers or meshes wrapped helically around a tubular body can be would such that the period or pitch of the helix changes along the axis of the helix such that regions with large helical spacing actuate at lower pressures as compared to regions of denser helical spacing. In other embodiments, the stiffness element(s) can include active elements such as magnetically-active, electro-active, thermally-active, or frequency-dependent polymers.

In yet other embodiments, the manufacturing module 1454 can include a device configured to actuate (e.g., inflate or deflate) the tubular body of the actuator during manufacturing to pre-tension or pre-compress mapped regions in the actuator as material is deposited or subtracted. Alternatively or in addition, machine(s) of the manufacturing module 1454 actuate or deflate the tubular body to a desired shape and a layer of stiff strain-limiting material is added to the surface to limit actuation in the local material region to that desired configuration.

In other optional embodiments, the manufacturing module 1454 is capable of assembling two (or more) material-mapped actuators in a desired fashion for completing a soft robot. For example, the manufacturing module 1454 can be configured to assemble two (or more) material-mapped actuators in series, optionally assembling or forming a valve (or valves) between the serially-connected material-mapped actuators. The valve(s) can take any of the forms described elsewhere in the present disclosure. In other embodiments, the manufacturing module 1454 is configured to integrally form a series of differently-configured material-mapped actuators each fluidly separated from one another by one or more valves using any of the manufacturing techniques described above. The so-formed valve can be a passive or active valve. In some non-limiting embodiments, the manufacturing module 1454 is configured to integrally or homogenously form, based upon the blueprint mapping described above two or more serially connected material-mapped actuators fluidly separated from one another by an asymmetric valve formed to exhibit a desired cracking pressure.

Using the foregoing specification, aspects of the present disclosure can be implemented as a machine, process or article of manufacture by using standard programming and/or engineering techniques to produce programming software, firmware, hardware or any combination thereof.

Any resulting program(s), having computer-readable instructions, may be stored within one or more computer-readable media such as memory devices or transmitting devices, thereby making a computer program product or article of manufacture according to the present disclosure. As such, the term "software" as used herein is intended to encompass a computer program existent as instructions on any non-transitory computer-readable medium such as on any memory device that are to be executed by a processor. Examples of memory devices include hard disk drives, optical disks, magnetic tape, semiconductor memories such as FLASH, RAM, ROM, PROMS, and the like.

A machine embodying aspects of the present disclosure may involve one or more processing systems including, for example, CPU, memory/storage devices, communication links, communication/transmitting devices, servers, I/O devices, or any sub-components or individual parts of one or more processing systems, including software, firmware, hardware, and any combination or subcombination thereof. Using the descriptions provided herein, those skilled in the art will be readily able to combine software created as described with appropriate general purpose or special purpose computer hardware to create a computer system and/or computer subcomponents embodying aspects of the present disclosure, and to create a computer system and/or computer subcomponents for carrying out methods of the present disclosure.

Figure 14:
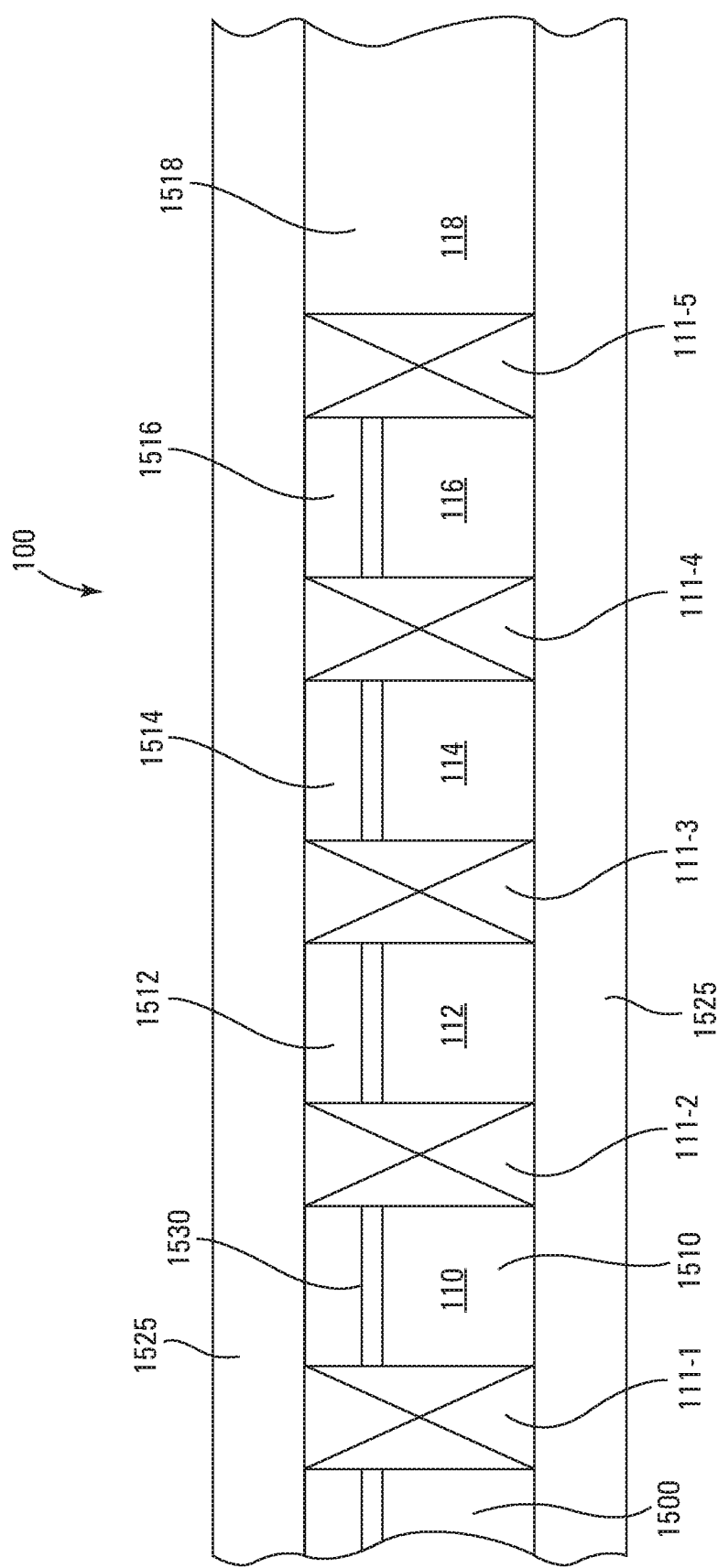
FIG. 14 illustrates an example of a robot having a pilot line in a main flow passage.

As mentioned above, in some embodiments, soft robots of the present disclosure can include or incorporate two or more actuators connected in series and fluidly separated by one or more valves. The valves of the present disclosure can assume various forms, several non-limiting example of which are described below. For example, FIG. 14 is a cross-sectional view (e.g., with cross-hatching omitted for clarity) of an example of robot 100, showing a main flow passage 1500 that includes hollow cores 1510, 1512, 1514, 1516, and 1518 respectively of sections 110, 112, 114, 116, and 118. In the example of FIG. 14, valve 111-1 selectively fluidly couples hollow core 1510 to the upstream pressure source, valve 111-2 selectively fluidly couples hollow cores 1510 and 1512, valve 111-3 selectively fluidly couples hollow cores 1512 and 1514, valve 111-4 selectively fluidly couples hollow cores 1514 and 1516, and valve 111-5 selectively fluidly couples hollow cores 1516 and 1518. Note that the working fluid flows through main flow passage 1500.

Main flow passage 1500 is bounded by a tube wall 1525 that includes the walls of sections 110, 112, 114, 116, and 118. In the example of FIG. 14, a pilot line 1530 interconnects valves 111-1 to 111-5 and supplies the pilot fluid to valves 111-1 to 111-5 for actuating valves 111-1 to 111-5. In some examples, pilot line 1530 might include (e.g., might be configured as) a rotary valve, such as a rotary valve 1911 discussed below in conjunction with FIGS. 18A-18D, or an axially sliding valve, such as axially sliding valve 2011 discussed below in conjunction with FIGS. 19A-19D. Note that for examples where the working fluid actuates valves 111-1 to 111-5, pilot line 1530 might be omitted from FIG. 14.

Figure 15:
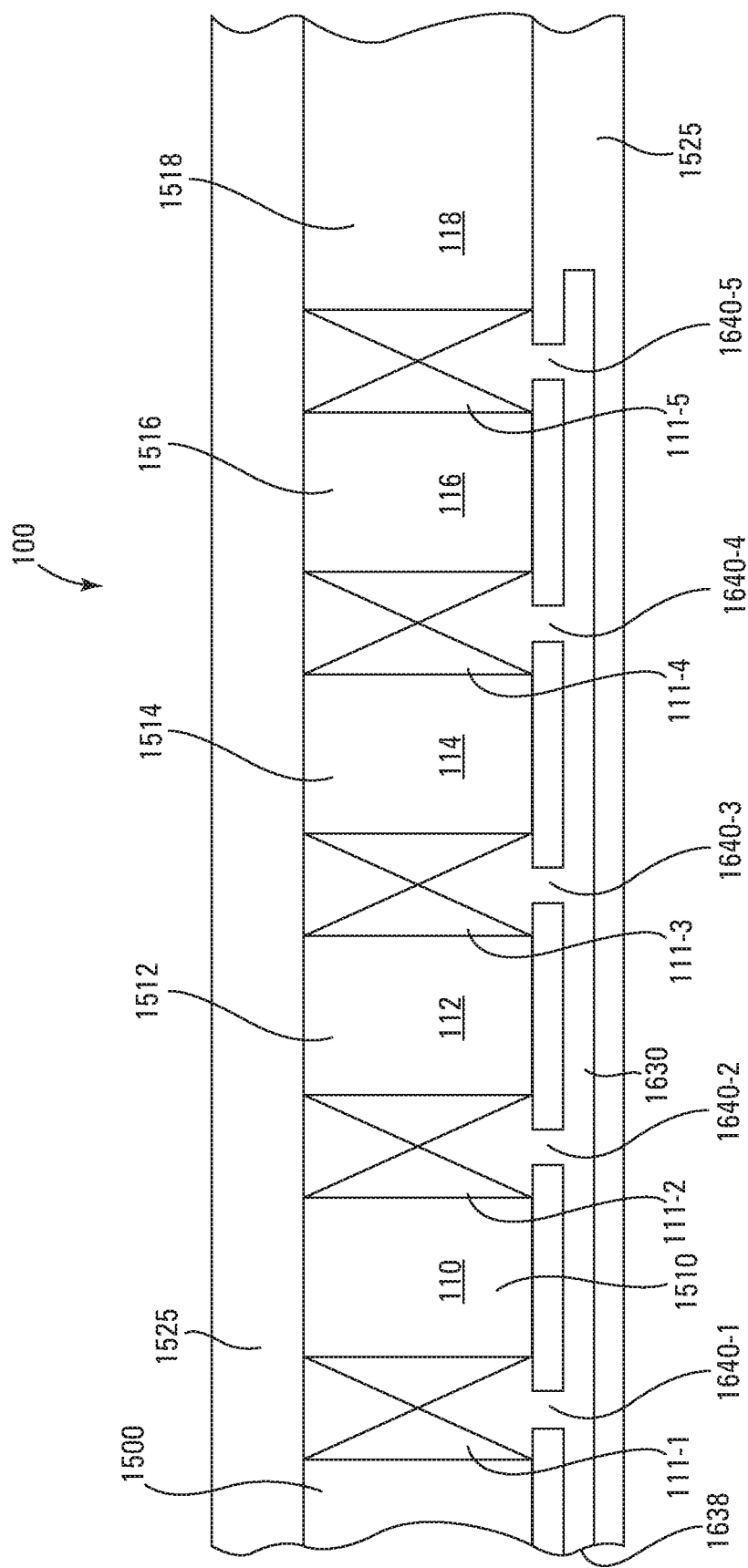
FIG. 15 illustrates an example of a robot having a pilot line in a wall.

FIG. 15 is a cross-sectional view (e.g., with cross-hatching omitted for clarity) of another example of robot 100. Common numbering is used in FIGS. 14 and 15 to denote elements common to FIGS. 14 and 15. In the example of FIG. 15, a pilot line 1630 is located in tube wall 1525. For example, pilot line 1630 might be configured as a manifold, e.g., having an opening (e.g., an inlet) 1638 and openings (e.g., outlets) 1640-1 to 1640-5 respectively coupled to valves 111-1 to 111-5 for directing the pilot fluid to valves 111-1 to 111-5. Alternatively, in some examples, pilot line 1630 might be configured as a rotary valve, such as the rotary valve 1911 discussed below in conjunction with FIGS. 18A-18D, or an axially sliding valve, such as the axially sliding valve 2011 discussed below in conjunction with FIGS. 19A-19D.

FIG. 16 is a cross-sectional view (e.g., with cross-hatching omitted for clarity) of another example of robot 100. Common numbering is used in FIGS. 14 and 16 to denote elements common to FIGS. 14 and 16. In the example of FIG. 16, pilot lines 1730-1 and 1730-2 are located in different portions of (e.g., at different circumferential locations in) tube wall 1525. For example, pilot line 1730-1 might be configured as a manifold, e.g., having an opening (e.g., an inlet) 1738-1 and openings (e.g., outlets) 1740-1 to 1740-3 respectively coupled to valves 111-1 to 111-3 for directing the pilot fluid to valves 111-1 to 111-3. Pilot line 1730-2, for example, might be configured as a manifold, e.g., having an opening (e.g., an inlet) 1738-2 and openings (e.g., outlets) 1740-4 and 1740-5 respectively coupled to valves 111-4 and 111-5 for directing the pilot fluid to valves 111-4 and 111-5. Alternatively, in some examples, each of pilot lines 1730-1 and 1730-2 might be configured as a rotary valve, such as the rotary valve 1911 discussed below in conjunction with FIGS. 18A-18D, or an axially sliding valve, such as the axially sliding valve 2011 discussed below in conjunction with FIGS. 19A-19D.

Figure 17A:
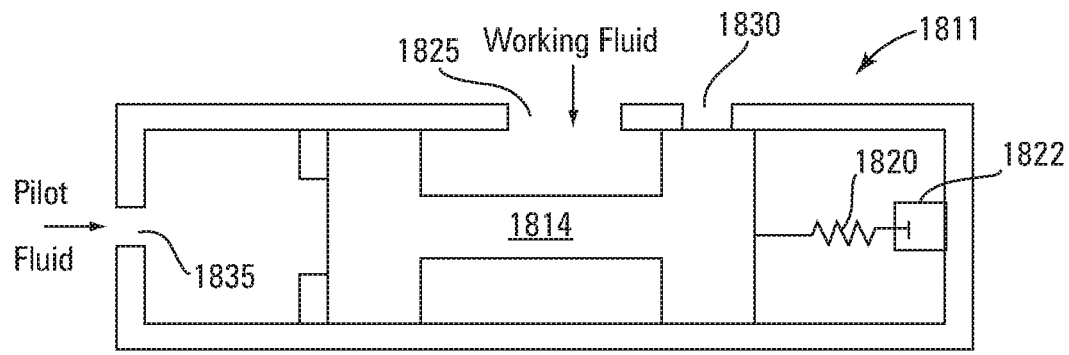
FIGS. 17A-17C illustrate an example of a valve at different states.
Figure 17B:
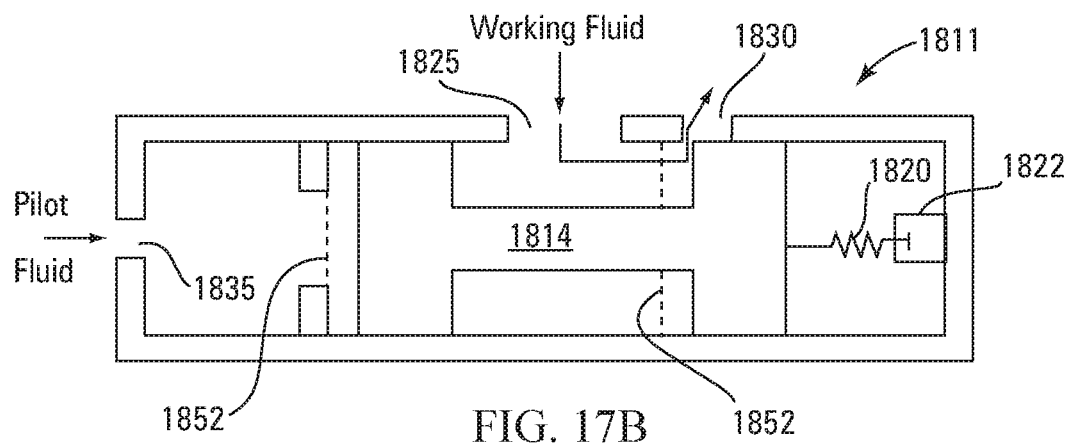
Figure 17C:
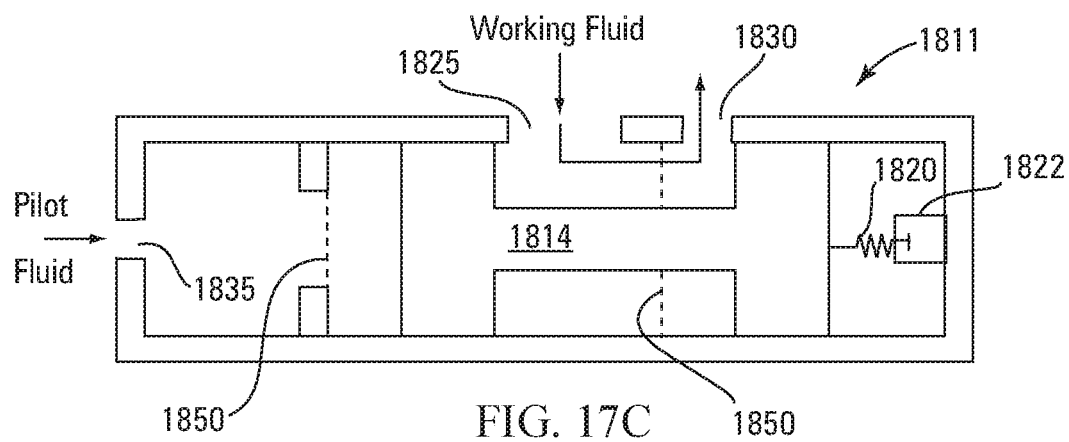

FIGS. 17A-17C illustrate an example of a valve 1811 at different states. Valve 1800 might be used for any of the valves 111-1 to 111-5. Valve 1811 is in a closed state in FIG. 17A. Valve 1811 includes a spool 1814 mechanically coupled to a spring 1820 that is mechanically coupled in series with a damper 1822. Valve 1811 includes an inlet port 1825 configured to receive the working fluid from upstream of valve 1811. For example, inlet port 1825 might receive the working fluid from the upstream pressure source or the hollow core of one of sections 110, 112, 114, or 116 of robot 100. Valve 1811 includes an outlet port 1830. In the closed state, spool 1814 completely covers (e.g., blocks) outlet port 1830. In some examples, valve 1811 includes a pilot port 1835 that receives the pilot fluid from a pilot line. However, pilot port 1835 might be omitted for examples where valve 1811 is actuated by the working fluid.

Outlet port 1830 might output the working fluid to the hollow core of section 110 when inlet port 1825 receives the working fluid from the upstream pressure source, to the hollow core of section 112 when inlet port 1825 receives the working fluid from the hollow core of section 110, to the hollow core of section 114 when inlet port 1825 receives the working fluid from the hollow core of section 112, to the hollow core of section 116 when inlet port 1825 receives the working fluid from the hollow core of section 114, or to the hollow core of section 118 when inlet port 1825 receives the working fluid from the hollow core of section 116.

In the example of FIG. 17A, valve 1811 receives either the working fluid with a fluctuating (oscillating pressure) or the pilot fluid with a fluctuating (oscillating pressure) at a non-resonant frequency of the spring 1820, spool (e.g., mass) 1814, damper 1822 system. For example, spool 1814 may remain stationary in the closed position shown in FIG. 17A while covering outlet port 1830 in response to the non-resonant frequency. That is, for example, valve 1811 remains closed in response to the non-resonant frequency.

In the example of FIG. 17C, valve 1811 receives either the working fluid with a fluctuating (oscillating pressure) at a resonant frequency of the spring 1820, spool (e.g., mass) 1814, damper 1822 system or the pilot fluid with a fluctuating (oscillating pressure) at a resonant frequency of the spring 1820, spool (e.g., mass) 1814, damper 1822 system. For example, valve 1811 may fully open in response to the resonant frequency.

For example, the resonant frequency causes spool 1814 to oscillate between the fully open position, where outlet port 1830 is completely uncovered by spool 1814, and, for example, the closed position of FIG. 17A, as indicated by the dashed lines 1850 in FIG. 17C. That is, for example, valve 1811 may oscillate between the fully closed and fully open states in response to the resonant frequency, where spool 1814 oscillates between the position where spool 1814 fully covers outlet port 1830 and the position where outlet port 1830 is fully uncovered by spool 1814 in response to the resonant frequency.

In the example of FIG. 17B, valve 1811 receives either the working fluid with a fluctuating (oscillating pressure) or the pilot fluid with a fluctuating (oscillating pressure) at a certain frequency of the spring 1820, spool (e.g., mass) 1814, damper 1822 system sufficient to cause spool 1814 to oscillate with a lower displacement than in response to the resonant frequency. For example, valve 1811 may partially open in response to the certain frequency.

For example, the certain frequency causes spool 1814 to oscillate between the partially open position, where outlet port 1830 is partially uncovered by spool 1814, and, for example, the closed position of FIG. 17A, as indicated by the dashed lines 1852 in FIG. 17B. That is, for example, valve 1811 may oscillate between the fully closed and partially open states in response to the certain frequency, where spool 1814 oscillates between the position where spool 1814 fully covers outlet port 1830 and the position where outlet port 1830 is partially uncovered by spool 1814 in response to the certain frequency. The certain frequency might be between the non-resonant frequency, e.g., in response to which spool 1814 remains covering outlet port 1830, and the resonant frequency, e.g., in response to which spool 1814 oscillates between where outlet port 1830 is completely uncovered by spool 1814 and where spool 1814 completely covers outlet port 1830.

Figure 17D:
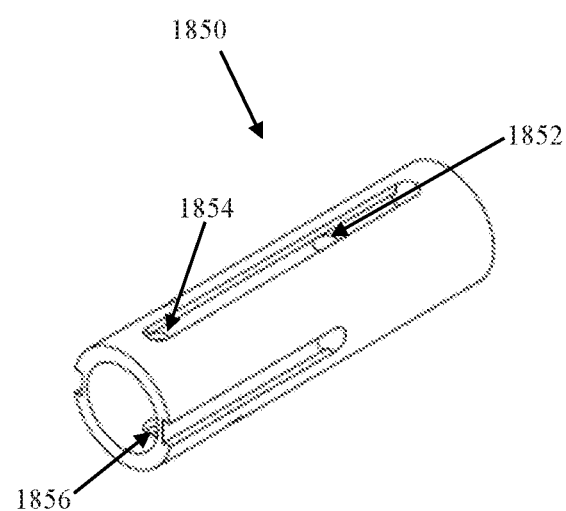
FIG. 17D is a perspective view of a bushing useful with the valve of FIGS. 17A-17C.

One non-limiting embodiment of a bushing 1850 useful with the optional spool valves of the present disclosure is shown in FIG. 17D. Bushing 1580 forms or defines one or more ports 1852-1856 that can be selectively covered and uncovered by an internally-carried spool (not shown).

Figure 18A:
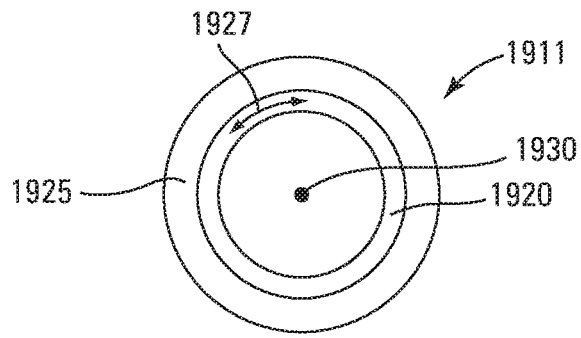
FIG. 18A illustrates an example of a rotary valve.
Figure 18B:
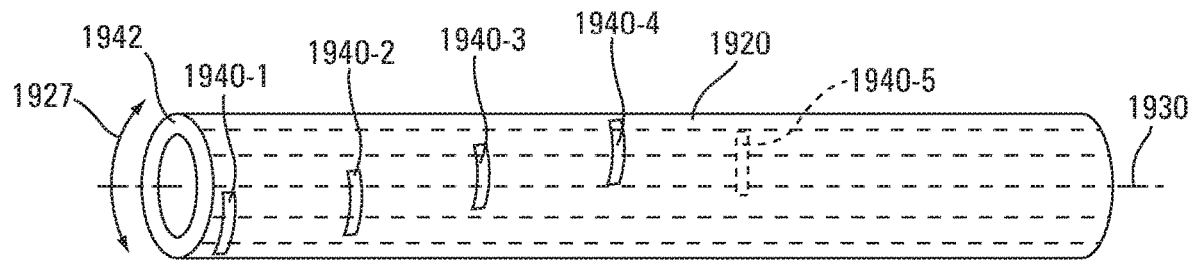
FIG. 18B illustrates an example of an inner portion of a rotary valve.
Figure 18C:
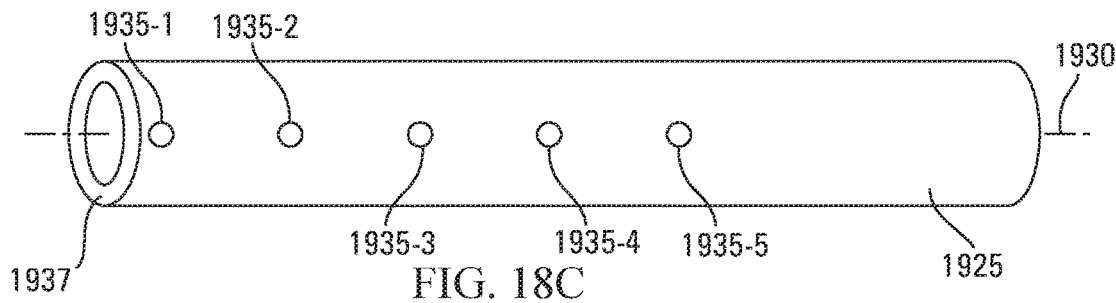
FIG. 18C illustrates an example of an outer portion of a rotary valve.

FIG. 18A illustrates an example of a rotary valve 1911 that includes an inner tube 1920 (FIG. 18B) and an outer tube 1925 (FIG. 18C). Inner tube 1920 is within outer tube 1925 so that inner tube 1920 and outer tube 1925 are coaxial about central axis 1930. Inner tube 1920 is configured to rotate within outer tube 1925, as indicated by arrows 1927 in FIGS. 18A and 18B, e.g., in response to rotational motion imparted to inner tube 1920, such as by a motor, a user (e.g., manually), etc.

Openings 1935-1 to 1935-5 (e.g., that might be circular openings) are distributed over the length of outer tube 1925, in the direction of central axis 1930, as shown in FIG. 18C, and pass through a wall 1937 of outer tube 1925. Openings 1940-1 to 1940-5 are distributed over the length of inner tube 1920, in the direction of central axis 1930, as shown in FIG. 18B, and pass through a wall 1942 of inner tube 1920. Openings 1940-1 to 1940-5 are elongated in a direction around the circumference of inner tube 1920. Openings 1940-1 to 1940-5 respectively correspond to openings 1935-1 to 1935-5 and respectively align with openings 1935-1 to 1935-5 when inner tube 1920 is respectively rotated to different angular locations.

Figure 18D:
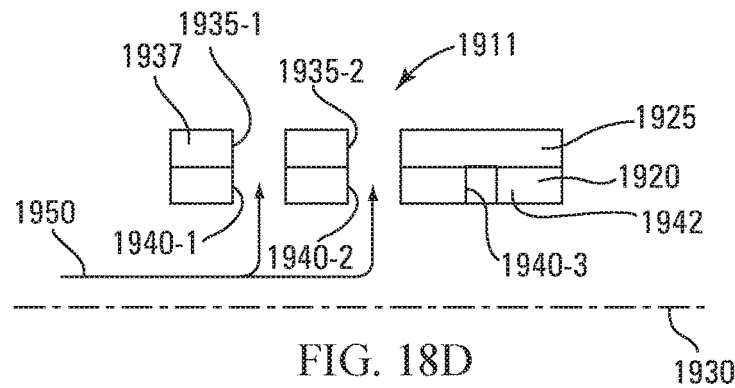
FIG. 18D illustrates a particular state of a rotary valve.

For example, FIG. 18D (a cross section of portions of tube wall 1937 of outer tube 1925 and of tube wall 1942 of inner tube 1920 with cross-hatching omitted for clarity) shows a particular state of valve 1911, where openings 1935-1 and 1940-1 and openings 1935-2 and 1940-2 are in alignment at a particular angular position of inner tube 1920. The concurrent alignment of openings 1935-1 and 1940-1 and openings 1935-2 and 1940-2 is facilitated by the elongation of openings 1940-1 and 1940-2, for example.

In some examples, openings 1935-1, 1935-2, 1935-3, 1935-4, and 1935-5 may be respectively fluidly coupled to the hollow cores of sections 110, 112, 114, 116, and 118. For example, when openings 1935-1 and 1940-1 are in alignment and openings 1935-2 and 1940-2 are in alignment at the particular angular location of inner tube 1920, working fluid flows through inner tube 1920, through aligned openings 1935-1 and 1940-1, and into the hollow core of section 110, and through aligned openings 1935-2 and 1940-2 and into the hollow core of section 112, as indicated by arrow 1950 in FIG. 18D.

In other examples, valve 1911 might be used to selectively direct pilot fluid to valves, such as valves 111-1, 111-2, 111-3, 111-4, and 111-5, so that the pilot fluid can actuate the valves. For example, openings 1935-1, 1935-2, 1935-3, 1935-4, and 1935-5 may be respectively fluidly coupled to valves 111-1, 111-2, 111-3, 111-4, and 111-5. When openings 1935-1 and 1940-1 are in alignment and openings 1935-2 and 1940-2 are in alignment at the particular angular location of inner tube 1920, for example, pilot fluid flows through inner tube 1920, through aligned openings 1935-1 and 1940-1, and to valve 111-1, and through aligned openings 1935-2 and 1940-2 and to valve 111-2, as indicated by arrow 1950 in FIG. 18D.

Valve 1911, and thus inner tube 1920 and outer tube 1925, may be within the main flow passage of robot 100 and may extend the entire length of robot 100. For example, the portions of valve 1911 respectively corresponding to openings 1935-1, 1935-2, 1935-3, 1935-4, and 1935-5 and openings 1940-1, 1940-2, 1940-3, 1940-4, and 1940-5 might be respectively in the hollow cores of sections 110, 112, 114, 116, and 118 and might respectively conform to the actuated shapes of sections 110, 112, 114, 116, and 118. That is, for example, the portion of valve 1911 corresponding to openings 1935-1 and 1940-1 might conform to the spiral shape of section 110; the portion of valve 1911 corresponding to openings 1935-2 and 1940-2 might extend with portion 112; the portion of valve 1911 corresponding to openings 1935-3 and 1940-3 might conform to the spiral shape of section 114; the portion of valve 1911 corresponding to openings 1935-4 and 1940-4 might twist with section 116; and the portion of valve 1911 corresponding to openings 1935-5 and 1940-5 might bend with section 118.

Figure 19A:
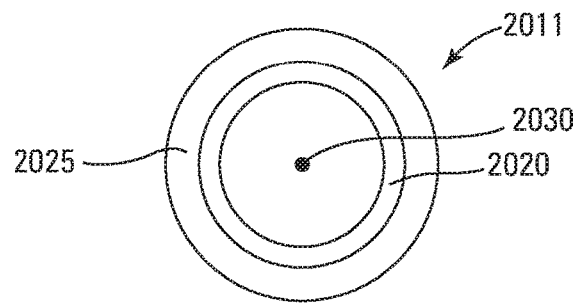
FIG. 19A illustrates an example of an axially sliding valve.
Figure 19B:
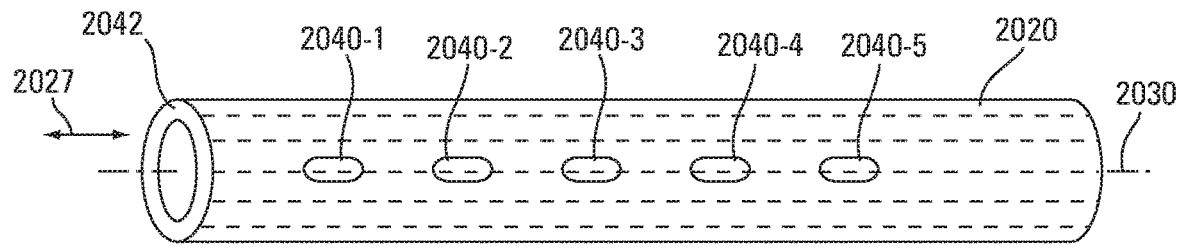
FIG. 19B illustrates an example of an inner portion of an axially sliding valve.
Figure 19C:
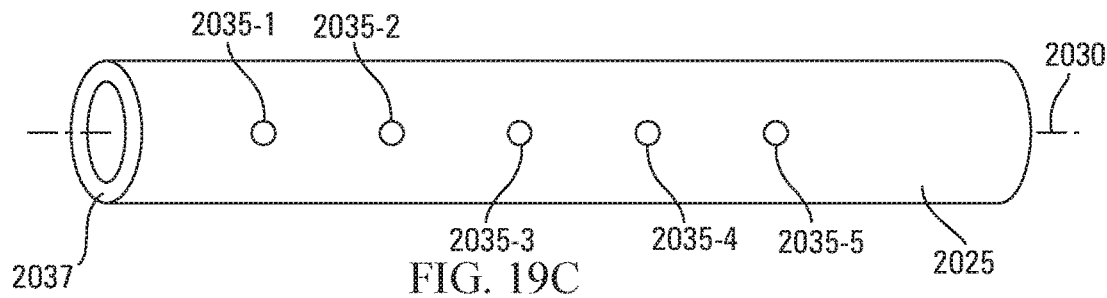
FIG. 19C illustrates an example of an outer portion of an axially sliding valve.

FIG. 19A illustrates an axially sliding valve 2011 that includes an inner tube 2020 (FIG. 19B) and an outer tube 2025 (FIG. 19C). Inner tube 2020 is within outer tube 2025 so that inner tube 2020 and outer tube 2025 are coaxial about central axis 2030. Inner tube 2020 is configured to slide in an axial direction (e.g., along central axis 2030) within outer tube 2025, as indicated by arrow 2027 in FIG. 19B, e.g., in response to axial motion imparted to inner tube 2020, such as by a motor, a user (e.g., manually), etc.

Openings 2035-1 to 2035-5 (e.g., that might be circular openings) are distributed over the length of outer tube 2025, in the direction of central axis 2030, as shown in FIG. 19C, and pass through a wall 2037 of outer tube 2025. Openings 2040-1 to 2040-5 are distributed over the length of inner tube 2020, in the direction of central axis 2030, as shown in FIG. 19B, and pass through a wall 2042 of inner tube 2020. Openings 2040-1 to 2040-5 are elongated in the axial direction. Openings 2040-1 to 2040-5 respectively correspond to openings 2035-1 to 2035-5 and respectively align with openings 2035-1 to 2035-5 when inner tube 2020 is respectively slid to different axial locations.

Figure 19D:
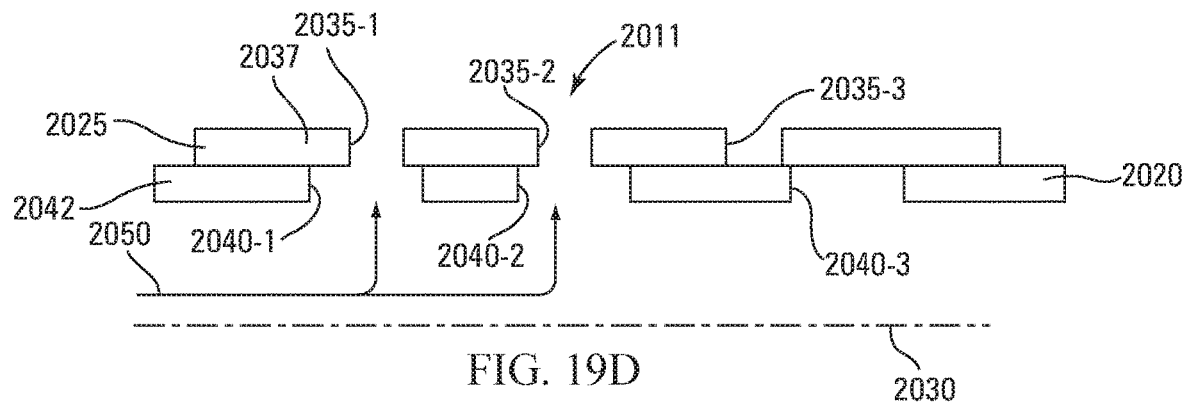
FIG. 19D illustrates a particular state of an axially sliding valve.

For example, FIG. 19D (a cross section of portions of tube wall 2037 of outer tube 2025 and of tube wall 2042 of inner tube 2020 with cross-hatching omitted for clarity) shows a particular state of axially sliding valve 2011, where openings 2035-1 and 2040-1 and openings 2035-2 and 2040-2 are in alignment at a particular axial position of inner tube 2020. The concurrent alignment of openings 2035-1 and 2040-1 and openings 2035-2 and 2040-2 is facilitated by the elongation of openings 2040-1 and 2040-2, for example.

In some examples, openings 2035-1, 2035-2, 2035-3, 2035-4, and 2035-5 may be respectively fluidly coupled to the hollow cores of sections 110, 112, 114, 116, and 118. For example, when openings 2035-1 and 2040-1 are in alignment and openings 2035-2 and 2040-2 are in alignment at the particular axial location of inner tube 2020, working fluid flows through inner tube 2020, through aligned openings 2035-1 and 2040-1, and into the hollow core of section 110, and through aligned openings 2035-2 and 2040-2 and into the hollow core of section 112, as indicated by arrow 2050 in FIG. 19D.

In other examples, valve 2011 might be used to selectively direct pilot fluid to valves, such as valves 111-1, 111-2, 111-3, 111-4, and 111-5, so that the pilot fluid can actuate the valves. For example, openings 2035-1, 2035-2, 2035-3, 2035-4, and 2035-5 may be respectively fluidly coupled to valves 111-1, 111-2, 111-3, 111-4, and 111-5. When openings 2035-1 and 2040-1 are in alignment and openings 2035-2 and 2040-2 are in alignment at the particular axial location of inner tube 2020, for example, pilot fluid flows through inner tube 2020, through aligned openings 2035-1 and 2040-1, and to valve 111-1, and through aligned openings 2035-2 and 2040-2 and to valve 111-2, as indicated by arrow 2050 in FIG. 19D.

Valve 2011, and thus inner tube 2020 and outer tube 2025, may be within the main flow passage of robot 100 and may extend the entire length of robot 100. For example, the portions of valve 2011 respectively corresponding to openings 2035-1, 2035-2, 2035-3, 2035-4, and 2035-5 and openings 2040-1, 2040-2, 2040-3, 2040-4, and 2040-5 might be respectively in the hollow cores of sections 110, 112, 114, 116, and 118 and might respectively conform to the actuated shapes of sections 110, 112, 114, 116, and 118. That is, for example, the portion of valve 2011 corresponding to openings 2035-1 and 2040-1 might conform to the spiral shape of section 110; the portion of valve 2011 corresponding to openings 2035-2 and 2040-2 might extend with portion 112; the portion of valve 2011 corresponding to openings 2035-3 and 2040-3 might conform to the spiral shape of section 114; the portion of valve 2011 corresponding to openings 2035-4 and 2040-4 might twist with section 116; and the portion of valve 2011 corresponding to openings 2035-5 and 2040-5 might bend with section 118.

Other valve constructions are also envisioned by the present disclosure. For example, an asymmetrical passive valve can be employed. One non-limiting example of an asymmetrical passive valve 2200 is shown in simplified form in FIG. 20A. The valve 2200 includes a cone 2202 arranged at a cone angle $\alpha$ relative to an outer wall 2204. The cone 2202 has a thickness T. The valve 2200 is configured to allow viscous flow restriction in addition to a cracking pressure in one direction that differs from cracking pressure in the opposite direction (i.e., the directions associated with the arrows "Forward Flow" and "Reverse Flow" in FIG. 20A). By varying one or both of the cone angle $\alpha$ and the cone thickness T, selection asymmetry is available. For example, FIG. 20B is a table of representative pressures for the valve 2200 (FIG. 20A) in the Forward Flow direction ($P_{fwd}$) and the Reverse Flow direction ($P_{rev}$) at various cone angles $\alpha$ and cone thicknesses T. FIG. 20C is a contour plot of the ratio ($P_{rev}/P_{fwd}-1$) for the valve 2200 (FIG. 20A). With cross-references between FIGS. 20A-20C, the valve 2200 can be constructed from a single elastomeric material where the design parameters such as thickness and cone angle can be used to tune the amount or level of asymmetry.

Further, in some embodiments, the valve structures and actuation thereof can incorporate pressure level indexing features (e.g., each valve open/closes at different ranges of pressure, like a multi-level relief valve). Valves that open at different differential pressures (e.g., sequencing valves, relief valves, etc.) can be used to connect the different sections or actuators; alternatively or in addition, two way differential pressure valves can be used to connect the different section or actuators. Alternatively, valves controlling each segment can have a linear or rotary sliding design, formed with an inner/outer sleeve arrangement in a pilot or main channel. The fit between the inner and outer sleeve can be a slight interference to a slight clearance, minimizing any fluid flow between the sleeves. The outer sleeve will have a series of holes in the wall that connect to the various actuation segments. The inner sleeve will also have a series of holes through the wall of the sleeve. The holes in the inner sleeve are arranged such that by translating and/or rotating the inner sleeve, the holes in the outer sleeve and inner sleeve will be aligned, opening the valve to one or more actuation segments. Both the inner and outer sleeves can flexible to the motion of the soft robot, but maintain axial alignment. This linear/rotary valve arrangement could be applied from a single pilot line (pressure supply) or two pilot lines (pressure supply and return). Regardless, each valve will be triggered at at-least-one different pressure differential, allowing each section to be actuated or unactuated sequentially and for a variety of pre-selected ranges.

For example, the first valve may open with a 10 psi pressure differential and the second valve at a 20 psi pressure differential. When the differential pressure across the first valve is greater than 10 psi fluid will fill the first actuator section and realize the spiral (or other) shape. Then, once a 20 psi threshold is reached across the second valve the second actuator section will fill with fluid and create the extension (or other) action. Each sequential valve will experience the same processes, but with the differential pressure value being increased for each valve. Since each valve can have multiple trigger thresholds, as the pressure increases some sections may experience a decrease in fluid level relative to others (e.g. the first spiral can collapse after the second has expanded and anchored in the tissue).

The valves may be opened/closed through temporal sequencing in some embodiments. This can be accomplished through dynamic or frequency variations of the input fluid. For example, time-dynamic input pressures conforming to a step or square-wave like input with passive flow restrictor valves can ensure that segments nearer the base actuate before segments further from the base. Temporal sequencing allows a valve to be toggled via pressure waves allowing for independent actuation of each section. Independent actuation allows for precise control of the soft robot (or other assembly incorporating three or more actuators of the present disclosure in series), each section can actuate or un-actuate to close in on the desired target. For example, the first valve can be latched partially open by experiencing a 50 Hz pressure wave, latched fully open by experiencing a 100 Hz pressure wave and latched closed by experiencing a 120 Hz pressure wave. The second valve will experience similar, selective actuation/latching via a different set of fluid pressure waves (e.g. 140, 160, and 180 or, if two sections need simultaneous valve actuation, 100, 160 and 180). It should be noted that many pressure waves can applied in superposition, thus enabling the simultaneous, independent control of all valves and actuation states. Additionally, valves can be designed not to latch but to continuously change state as a function of the frequency or amplitude of the waves. For example, a valve will fully close at 50 Hz and fully open at 100 Hz, but can partially open to a desired level at a frequency in between 50 and 100 Hz. For example, a valve will be 50% open at 75 Hz. Similarly, the 50 Hz drives a valve to close and 100 Hz drives it to open (e.g., a binary open/close) then the presence of both waves at equal amplitude may effectively cause the valve to behave as if it were partially closed/open.

With the optional pressure level indexing embodiments described above, a pilot line can be used to control each valve state. Pressure signals can be sent through the pilot line to control the state of each valve. Each valve will respond to a unique pressure or frequency, which will result in a change of flow in the main channel. For example, the pressure signal(s) can be constant amplitude pressure commands to act as a pilot signal to valves controlling various actuators. Alternatively, the frequency of the pressure in the pilot line can be used to open and close the valves controlling the various actuators. In yet other embodiments, the pilot line valves can be combined with an inflow and outflow channel, with the pilot line controlling four states of the inflow/outflow channel as: State 1) inflow and outflow both closed; State 2) inflow open and outflow closed; State 3) inflow and outflow both open; and State 4) inflow closed and outflow open.

The soft robots and actuators (including material-mapped actuators) of the present disclosure can be highly beneficial in a plethora of different end-use applications, procedures or tasks. For examples, the soft robots and actuators (including material-mapped actuators) can be designed and employed to perform procedures within the human body, for example through or within blood vessels (e.g., ranging in diameter from 10 mm (femoral artery) to 1 mm (stenosed coronary artery)). The soft robots and actuators of the present disclosure can safely traverse blood vessels via the locomotion-type shape change features described above without hindering blood flow and exerting minimal force on vessel walls. By incorporating the optional worm-like design or locomotion effect, the soft robots and actuators of the present disclosure can "pull" themselves through arteries at a lower force than stiffer, "pushed" catheters and can conform to the tightest, most tortuous regions of a patient's vasculature.

Figure 21:
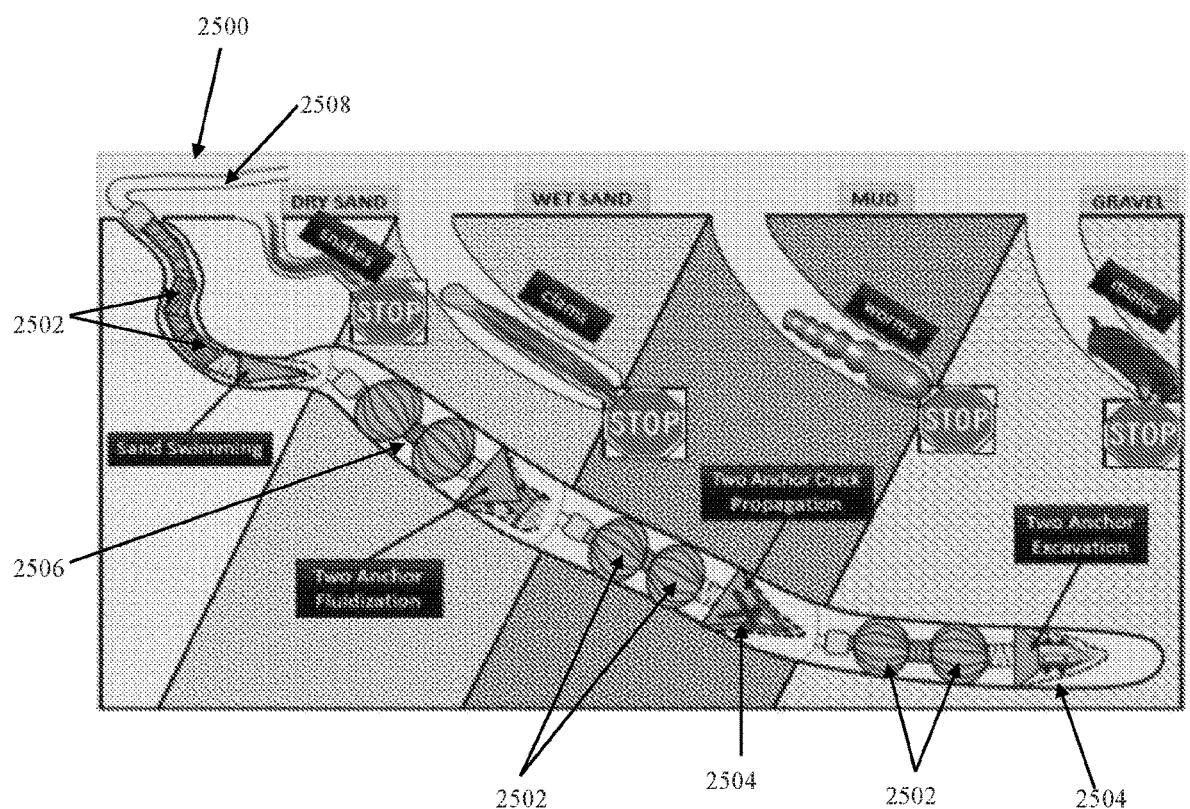
FIG. 21 is a simplified view of another soft robot in accordance with principles of the present disclosure traversing through various types of soil.

The soft robots and actuators (including material-mapped actuators) can alternatively be configured or designed for other end-use applications, procedures or tasks, such as burrowing though soils and other materials. Soft robots of the present disclosure can be capable of generating multiple burrowing motions as describe above, and thus can entail adaptive gait change and burrow penetration mechanisms to enable efficient and precision burrowing through a wide variety of soil types. As a point of reference, FIG. 21 illustrates, in simplified form, the locomotion gait and penetration mechanism utilized by nature to burrow through differing soil types (dry sand, wet sand, mud, and gravel). A soft robot 2500 in accordance with principles of the present disclosure can be constructed to replicate or mimic each of the discrete locomotion gaits implicated by a particular end-use application. For example, the soft robot 2500 can include one or more material-mapped actuators (referenced generally at 2502) described above designed to sequentially or responsively replicate a desired locomotive gait, along with one or more heads 2504 configured to provide or effectuate a desired penetration mechanism. The material-mapped actuators 2502 can be independently controlled by internal valves 2506 fed from a common pressure rail 2508. The soft robot 2500 can be constructed to effectuate one or more of blunt penetration (to burrow through dry sand), fluidization (to burrow through wet sand), crack propagation (to burrow through mud), and/or excavation (to burrow through gravel, compact dirt, etc.). The locomotion gait(s) incorporated into the soft robot 2500 can be premised upon the two dominant burrowing gaits observed in nature, undulation and alternate anchoring, into the fundamental motion primitives.

In some embodiments, the soft robot 2500 (configured for burrowing through multiple types of soil) can include one or more sensors that provide information indicative of position, soil type, impediments to movement, etc. For example, carbon-nanotube elastomer sensors can be included that provide accurate measurements for links of the soft robot 2500 (position errors under 5% of the surface length using 2D multiplexed ratiometric; force of contact error <20% using contact resistance and <5% using piezo resistive effects after viscoelastic calibration). Sensing can be provided of the internal robot state, location of contact along the outer surface or skin of the soft robot 2500 and/or position of this contact. An accurate dynamic material analyzer (e.g., 300 Hz Bandwidth analyzer available under the trade designation Bose ElectroForce 3200 Series III) can be employed to characterize the uniaxial piezo-resistive pseudoelastic dynamic response of the carbon-nanotube sensor to construct a tractable nonlinear dynamic model for calibrating the sensor and quantify its accuracy and repeatability. Mathematical models can be implemented as code on an embedded processor in the sensor electronics to allow for repeatable, accurate real-time measurement of forces or pressures applied to the sensor (that is otherwise located at a link of the soft robot 2500).

Although specific examples have been illustrated and described herein, this application is intended to cover any adaptations or variations of these examples. It is manifestly intended that the scope of the claimed subject matter be limited only by the following claims and equivalents thereof.

What is claimed is:

1. A material-mapped actuator for use as a soft robot, the actuator comprising:
    an actuator body defining a length; and
    a pattern formed along the actuator body, the pattern being non-uniform across the length;
    wherein the actuator incorporates a spatially-varying map of mechanical properties that spatially vary along a coordinate system of the actuator body;
    and further wherein the actuator defines an initial state having an initial shape with a corresponding map of mechanical attributes consisting of locally-varying stiffness at each point in a volume of the actuator body;
    and even further wherein the actuator is configured to transition from the initial state to a second state upon distribution of an actuation medium within the body as a function of the spatially-varying map of mechanical properties, the second state differing from the first state by at least one of:
        the second state defines a second shape differing from the first shape, and
        the second state has a distribution of mechanical properties differing from the first state.

2. The actuator of claim 1, wherein the pattern is formed by a body material.

3. The actuator of claim 2, wherein the body material includes an elastomer.

4. The actuator of claim 2, wherein the body material includes a combination of elastomers formed by one of locally continuous mixtures and locally discrete combinations such that local mechanical properties are provided at selected points.

5. The actuator of claim 2, wherein the body material includes at least one local, spatially-varying additive material selected from the group consisting of: locally-oriented fiber, mesh, thread, fiberglass, carbon black, carbon fiber, knitted material, and woven material.

6. The actuator of claim 5, wherein the additive is configured to influence different regions of the local material stress-strain curve by being at least one of pre-stretched, pre-compressed and pre-bunched.

7. The actuator of claim 5, wherein the additive material does not continuously span an entire length of the actuator body.

8. The actuator of claim 1, wherein the actuator is configured to actuate in response to the actuation medium in form of a volume of fluid, and further wherein the work done by the fluid induces a stretching force along a surface of the actuator and the spatially varying stiffness induces a desired change in at least one of an overall shape and an externally applied force.

9. The actuator of claim 1, wherein at least one of the mapped properties includes specified local volumes of active material that change in size in spatially-dependent magnitudes due to an applied stimulus selected from the group consisting of electric, magnetic, electromagnetic, thermal, mechano-vibrational, acoustic, and optic stimuli.

10. The actuator of claim 1, wherein the actuator is configured to actuate in sequence from the initial state to an intermediate state having a pre-determined intermediate shape differing from the initial shape, and from the intermediate state to a final state having a final shape differing from the intermediate shape.

11. The actuator of claim 1, wherein the actuator body is a circular tube.

* * * * *